United States Patent
Di Fiore

(10) Patent No.: US 8,057,439 B2
(45) Date of Patent: Nov. 15, 2011

(54) CARDIOVASCULAR ACCESS CATHETER WITH SLIT VALVE

(75) Inventor: Attilio E. Di Fiore, Taylorsville, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 12/371,570

(22) Filed: Feb. 13, 2009

(65) Prior Publication Data
US 2009/0149820 A1   Jun. 11, 2009

Related U.S. Application Data

(62) Division of application No. 11/027,040, filed on Dec. 30, 2004, now Pat. No. 7,491,192.

(51) Int. Cl.
*A61M 5/178* (2006.01)
*A61M 5/00* (2006.01)
(52) U.S. Cl. .................... 604/167.04; 604/247
(58) Field of Classification Search ............ 604/167.04, 604/99.03, 246–248
See application file for complete search history.

(56) References Cited

U.S. PATENT DOCUMENTS

| | | | |
|---|---|---|---|
| 3,020,913 A | 2/1962 | Heyer | |
| 4,549,879 A | 10/1985 | Groshong et al. | |
| 4,559,046 A | 12/1985 | Groshong et al. | |
| 4,634,427 A | 1/1987 | Hannula et al. | |
| 4,671,796 A | 6/1987 | Groshong et al. | |
| 4,701,166 A | 10/1987 | Groshong et al. | |
| 4,737,152 A | 4/1988 | Alchas | |
| 4,753,640 A | 6/1988 | Nichols et al. | |
| 4,973,319 A | 11/1990 | Melsky | |
| 4,995,863 A * | 2/1991 | Nichols et al. | 604/247 |
| 5,004,455 A | 4/1991 | Greenwood et al. | |
| 5,030,210 A | 7/1991 | Alchas | |
| 5,084,015 A | 1/1992 | Moriuchi | |
| 5,112,301 A | 5/1992 | Fenton, Jr. et al. | |
| 5,147,318 A | 9/1992 | Hohn | |
| 5,147,332 A * | 9/1992 | Moorehead | 604/247 |
| 5,160,325 A | 11/1992 | Nichols et al. | |
| 5,169,393 A | 12/1992 | Moorehead et al. | |
| 5,201,722 A | 4/1993 | Moorehead et al. | |
| 5,205,834 A | 4/1993 | Moorehead et al. | |
| 5,215,527 A | 6/1993 | Beck et al. | |
| 5,224,938 A * | 7/1993 | Fenton, Jr. | 604/247 |
| 5,250,034 A | 10/1993 | Appling et al. | |
| 5,261,885 A | 11/1993 | Lui | |
| 5,304,155 A | 4/1994 | Lui | |
| 5,405,334 A | 4/1995 | Roth et al. | |
| 5,460,618 A | 10/1995 | Harreld | |
| 5,522,807 A | 6/1996 | Luther | |

(Continued)

*Primary Examiner* — Nicholas Lucchesi
*Assistant Examiner* — Jenna Zhang
(74) *Attorney, Agent, or Firm* — Rutan & Tucker, LLP

(57) ABSTRACT

Two-way, three-position and one-way, two-position slit valves in cardiovascular access catheters with closed distal ends have slit geometries configured to overcome adhesion between opposed abutting slit faces, when pressure differentials are applied between the interior and the exterior of the catheter. Portions of the slit are oriented at a non-zero angle relative to the longitudinal axis of the catheter causing shear forces to be generated in abutting slit faces. Shear forces arise from tangential, radial, or longitudinal stresses generated in the catheter body. Slit geometries are planar or curved or include multiple end-to-end connected slit subsections. If a slit partially circumscribes a portion of the adjacent outer wall of the catheter body, restraint to outward and inward movement on that portion is reduced. Slit valves are configured to open inwardly to aspirate fluids, to open outwardly to infuse fluids, or both.

14 Claims, 21 Drawing Sheets

U.S. PATENT DOCUMENTS

| | | |
|---|---|---|
| 5,533,986 A | 7/1996 | Mottola et al. |
| 5,554,136 A | 9/1996 | Luther |
| 5,776,096 A | 7/1998 | Fields |
| 5,807,349 A * | 9/1998 | Person et al. .................. 604/247 |
| 5,810,789 A | 9/1998 | Powers et al. |
| 5,843,044 A | 12/1998 | Moorehead |
| 5,928,203 A | 7/1999 | Davey et al. |
| 5,984,902 A | 11/1999 | Moorehead |
| 5,984,903 A | 11/1999 | Nadal |
| 6,293,958 B1 * | 9/2001 | Berry et al. .................... 606/191 |
| 2004/0102738 A1 * | 5/2004 | Dikeman et al. ............... 604/256 |
| 2005/0043703 A1 | 2/2005 | Nordgren |

* cited by examiner

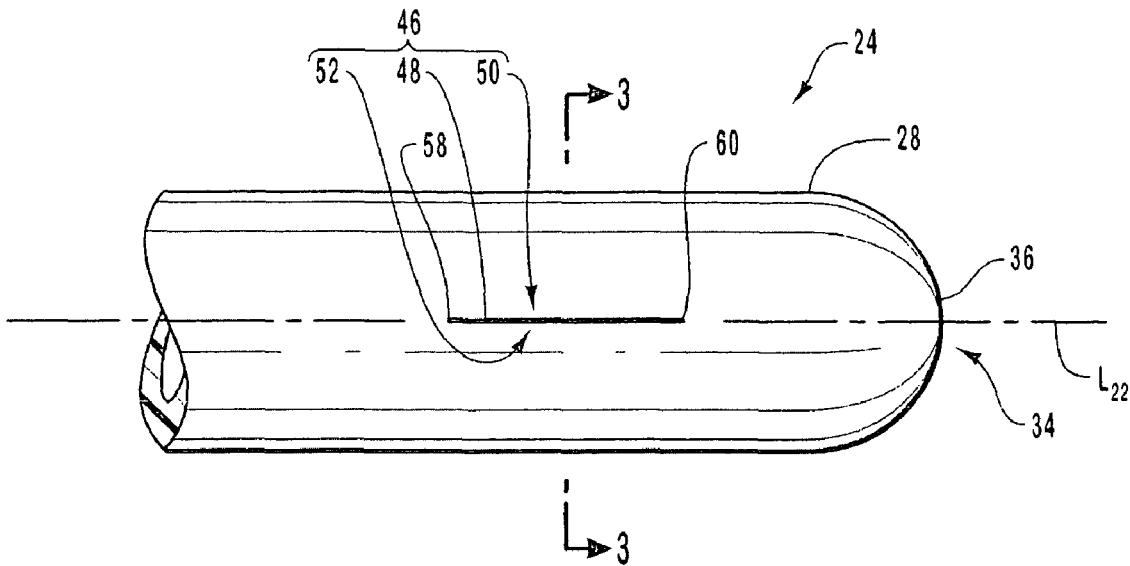
FIG. 2
(PRIOR ART)
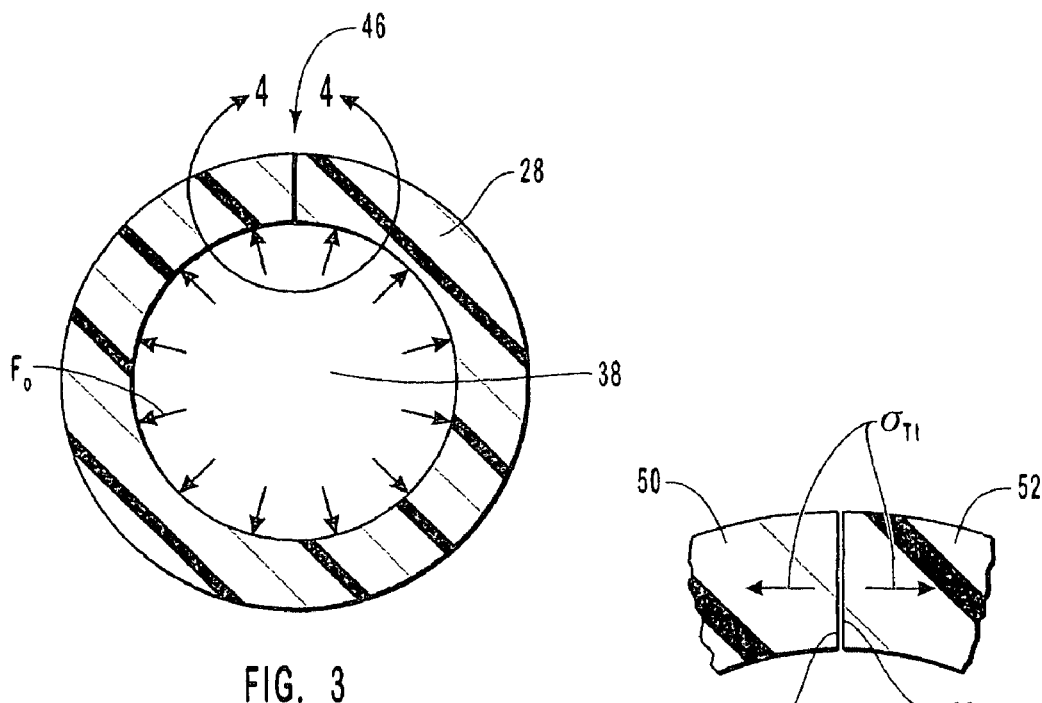
FIG. 3
(PRIOR ART)
FIG. 4
(PRIOR ART)

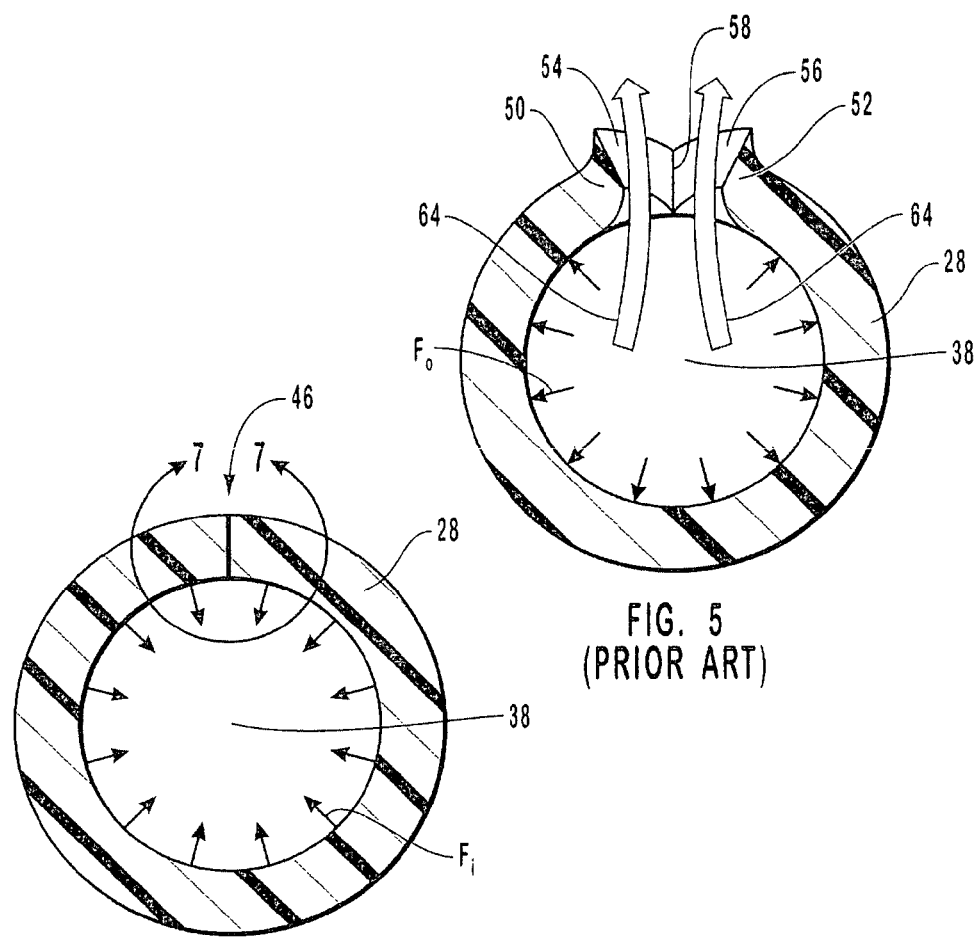
FIG. 5 (PRIOR ART)
FIG. 6 (PRIOR ART)
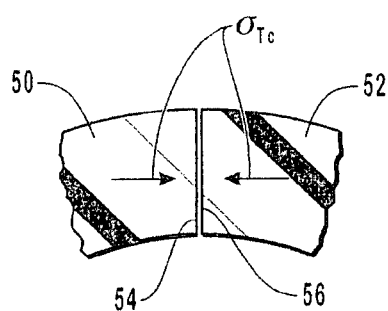
FIG. 7 (PRIOR ART)
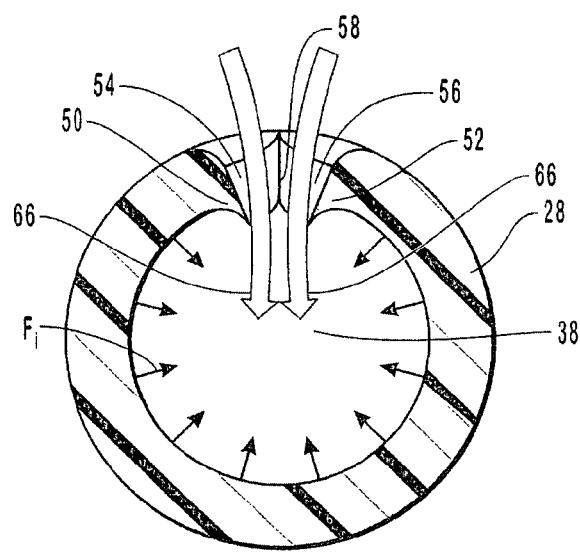
FIG. 8 (PRIOR ART)

CARDIOVASCULAR ACCESS CATHETER WITH SLIT VALVE

PRIORITY

This application is a division of U.S. patent application Ser. No. 11/027,040, filed Dec. 30, 2004, now U.S. Pat. No. 7,491,192, each of which is incorporated into this application as if fully set forth herein.

BACKGROUND

1. Field of the Invention

This invention pertains to medical catheters, and more particularly to catheters adapted for transcutaneous or complete implantation in the body of a human patient, thereby to provide access through the catheter to the cardiovascular system of the patient.

2. State of the Art

Catheters are commonly used to access the cardiovascular system of a patient from outside the body of the patient. The cardiovascular access afforded by such catheters permits the monitoring of blood pressure, the aspiration of blood, and the infusion of medicaments and nutrients at various locations within the cardiovascular system. For example, catheters can provide access to the central regions of the cardiovascular system in the vicinity of the high volume blood flow passageways immediately interconnected with the heart.

Cardiovascular access catheters typically include an elongated, flexible catheter tube having one or more fluid flow passageways, or lumens, extending longitudinally therethrough to an open end of the catheter. During implantation in the body of a patient, the open end of the catheter is inserted through an incision in the skin into a blood vessel of the cardiovascular system. This inserted end is referred to as the distal end of the catheter, while the opposite end is referred to as the proximal end of the catheter. The distal end of the catheter is advanced through the blood vessels of the cardiovascular system to a predetermined location at which intended therapeutic activity is to be conducted. The portion of the length of the catheter proximate the distal end thereof resides in contiguous blood vessels of the cardiovascular system. The catheter extends through an incision in the skin of the patient at a location remote from the predetermined location at which therapy is conducted and remote from delicate viscera. An extracorporeal portion of the catheter, which includes the proximal end, is located outside the body of the patient and is accessible to medical practitioners. Medication or nutrients are introduced into the proximal end of the catheter and delivered to the predetermined location in the body of the patient through the open distal end of the catheter body. The open distal end of the catheter body provides a permanent opening through which fluid communication is continuously maintained between the lumen or lumens in the catheter body and the cardiovascular system of the patient.

When the catheter is being used for therapeutic purposes, it is necessary to establish continuous fluid communication through the catheter between the proximal end of the catheter and the interior of the body of a patient. When the catheter is not being used, however, this continuous fluid communication is undesirable and dangerous. The pathway along which this continuous fluid communication is established provides a route by which infection can enter into the body of the patient. The pathway is also a conduit through which fluid can uncontrollably escape from the cardiovascular system of the patient, or through which air can enter into the cardiovascular system of the patient. Therefore, the continuous fluid communication to the cardiovascular system provided by the catheter must be curtailed when the catheter is not in use.

One method of curtailing the continuous fluid communication provided by the catheter involves clamping the extracorporeal portion of the catheter body with a tube clamp. A tube clamp can impose undesirable wear on a catheter body and may be released unintentionally. In addition, while a tube clamp prevents net fluid flow through the catheter, a tube clamp does not prevent fluid transfer between the cardiovascular system of the patient and the lumen of the catheter body through the open distal end thereof. The lumen of a cardiovascular access catheter is filled with a relatively static column of fluid when the catheter is not in use. If a catheter has a permanently open distal end, constituents of body fluid diffuse into that column of fluid through the open end when the catheter is not in use, even though access to the cardiovascular system through the catheter has been curtailed by clamping the extracorporeal portion of the catheter.

Small volumes of blood might enter the stagnant column of fluid and clot, possibly leading to various complications that are dangerous to the patient. The clotting process can completely obstruct the otherwise permanently open distal end of the catheter or the interior of the associated lumen. An obstruction renders the catheter useless and requires removal of the obstructed catheter and implantation of a replacement catheter. When the catheter lumen is only partially obstructed by the clot, the risk to the patient can be severe. Fluid forced through a partially obstructed lumen may flush the clot out from the lumen into the cardiovascular system of the patient. Inside the cardiovascular system, the clot can obstruct blood vessels and contribute to a heart attack, a pulmonary embolism, or a stroke.

To minimize the dangers associated with clots, cardiovascular access catheters have been provided with closed distal ends and selectively operable valve structures formed through the catheter body near the distal ends thereof. These valve structures open during therapeutic fluid infusion or aspiration, but remain closed when the catheters are not in use. A valve structure developed for this purpose takes the form of a longitudinally extending planar slit formed through the outer wall of a catheter tube having a closed distal end. The slit extends from the exterior of the catheter through the closed distal end or through the circumferential outer wall of the catheter body to a lumen in the catheter body. On either side of the slit, portions of the outer wall of the catheter body are formed by the slit into a first valve wall and a second valve wall. The first valve wall terminates at the slit in a first slit face. The second valve wall terminates at the slit in a second slit face that is congruent to the first slit face. When the valve is in the closed position thereof, the planar slit faces are opposed to and in abutment with one another, meeting in what will henceforth be referred to for convenience of discussion as a slit orientation plane. The opposed faces of the slit normally remain in abutting sealing engagement, isolating the column of fluid in the associated lumen from the region in the body of the patient outside the catheter tube in the vicinity of the slit valve.

FIGS. 1-8 depict a cardiovascular access catheter device 20 that includes such a known slit valve structure.

FIG. 1 is a perspective view of cardiovascular access catheter device 20 implanted in the body of a patient 10 for whom a therapeutic procedure is to be undertaken on an intermittent basis, by way of example, in superior vena cava 12 of the venous subsystem of the cardiovascular system. Catheter device 20 includes a soft, biocompatible, single lumen catheter body 22 having a distal portion 24 that is intended to reside in superior vena cava 12 and a proximal end 26 that resides outside the body of patient 10. A significant portion of catheter body 22 proximate distal portion 24 resides in the contiguous blood vessels extending away from superior vena cava 12. In the vicinity of shoulder 14 of patient 10, a section of catheter body 22 extends through an incision in the skin between the blood vessels and the exterior of the body of patient 10. Proximal end 26 of catheter body 22 carries a tubing clamp 42 and terminates in a luer connector 40 that can be selectively coupled to extracorporeal medical equipment.

Alternatively, proximal end 26 of catheter body 22 could be attached to a subcutaneously implantable access port, and the entire length of catheter body 22 and the access port could be implanted within the body of patient 10. In this configuration, the entire device is implanted in the body, and no extracorporeal portion is provided.

FIG. 2 is an enlarged plan view of distal portion 24 of catheter body 22 of FIG. 1. Catheter body 22 at distal portion 24 thereof is seen to have a longitudinal axis $L_{22}$ and to terminate in a closed distal tip 34. Distal portion 24 of catheter body 22 has a cylindrical circumferential outer wall 28 and a semispherical terminal endwall 36 that is continuous with outer wall 28. A slit valve 46 is formed in outer wall 28 near terminal endwall 36. Slit valve 46 includes a planar slit 48 that extends longitudinally along outer wall 28 parallel to longitudinal axis $L_{22}$ of catheter body 22. Planar slit 48 separates a first valve wall 50 from a second valve wall 52 that are otherwise integrally formed with outer wall 28 of catheter body 22, except at planar slit 48.

FIG. 3 is a transverse cross-sectional view of distal portion 24 of catheter body 22 illustrated in FIG. 2 taken along section line 3-3 shown therein. Outer wall 28 is seen to enclose a single lumen 38. FIG. 4 is an enlarged detail view of the portion of the cross section of FIG. 3 depicting slit valve 46. First valve wall 50 terminates in a first slit face 54, and second valve wall 52 terminates in a second slit face 56 that is congruent with first slit face 54.

Slit valve 46 functions as a reliable two-way, three-position valve. In the closed position of slit valve 46 shown in FIGS. 2 and 3, first slit face 54 and second slit face 56 of slit valve 46 are in abutting and sealing engagement. Fluid is precluded from entering or exiting lumen 38 of catheter device 20 through slit valve 46 in the closed position of slit valve 46.

To move slit valve 46 into an outwardly open position, positive pressure is applied to the static column of fluid occupying lumen 38. This pressure creates a positive pressure differential between lumen 38 on one side of slit valve 46 and the region in the body of patient 10 on the other side of slit valve 46. FIG. 3 illustrates outwardly-directed forces $F_o$ acting on outer wall 28 of catheter body 22 that are generated by the positive pressure differential. FIG. 4 illustrates that in the process depicted in FIG. 3, a circumferentially applied tangential tensile stress $\sigma_{Tt}$ is generated in outer wall 28 by forces $F_o$. Tangential tensile stress $\sigma_{Tt}$ causes first slit face 54 and second slit face 56 to separate out of abutting, sealing engagement in the manner shown in FIG. 4. Once first slit face 54 and second slit face 56 are out of abutting, sealing engagement, forces $F_o$ cause first valve wall 50 and second valve wall 52 to open outwardly as shown in FIG. 5 into the outwardly open position of slit valve 46. Fluid 64 is infused from lumen 38 into the cardiovascular system of patient 10 as shown in FIG. 5 due to the positive pressure differential. If the pressure differential between lumen 38 and the region in the cardiovascular system of patient 10 on the other side of slit valve 46 is reduced to a threshold level, first slit face 54 and second slit face 56 will again assume the closed position of slit valve 46 shown in FIG. 3 and resume abutting, sealing engagement.

To move slit valve 46 into an inwardly open position, a negative pressure or suction is applied to the static column of fluid contained within lumen 38 from proximal end 26. This suction generates a negative pressure differential between lumen 38 on one side of slit valve 46 and the region in the body of patient 10 on the other side of slit valve 46. FIG. 6 illustrates inwardly-directed forces $F_i$ acting on outer wall 28 of catheter body 22 that are generated by the negative pressure differential. Slit valve 46 is shown in the closed position thereof in FIG. 6. FIG. 7 illustrates that in the process depicted in FIG. 6, a circumferentially applied tangential compressive stress $\sigma_{Tc}$ is generated in outer wall 28 by forces $F_i$. Forces $F_i$ cause first valve wall 50 and second valve wall 52 to open inwardly as shown in FIG. 8 into the inwardly open position of slit valve 46. Fluid 66 is aspirated into lumen 38 from the cardiovascular system of patient 10 as shown in FIG. 8 due to the negative pressure differential. If the negative pressure differential is reduced to a threshold level, first slit face 54 and second slit face 56 will again assume the closed position of slit valve 46 shown in FIG. 6 and resume abutting, sealing engagement.

At the extreme ends of slit valve 46 shown in FIG. 2, opposed first slit face 54 and second slit face 56 meet at a proximal slit end line 58 and a distal slit end line 60 shown on end in FIG. 2 that extend radially through catheter body 22. The extreme ends of slit valve 46 do not separate during aspiration or infusion. Thus, the inward or outward deflection of first valve wall 50 and second valve wall 52 of slit valve 46 occurs, not to a uniform extent along the length of planar slit 48, but to an extent that ranges from a maximum at the center of the length of planar slit 48 to a minimum at a distance away from that center in the direction of each of proximal slit end line 58 and distal slit end line 60.

The development of a reliable two-way, three-position slit valve formed in the circumferential outer wall of a catheter has solved many problems associated with catheters having permanently open apertures in the distal end of the catheter body that resides inside the cardiovascular system of the patient.

Historically, cardiovascular access catheters with slit valves have been made from medical grade silicone materials. Silicone materials are soft, flexible through a wide range of temperatures, and free of clinically harmful, leachable plasticizers. Silicone materials are resistant to chemicals, relatively non-thrombogenic, and atraumatic to surrounding tissues, all of which contribute to high biostability and biocompatibility. In addition, silicone materials may be sterilized by ethylene oxide gas, gamma or electron beam radiation, or steam autoclaving.

A catheter must have sufficient wall thickness to prevent tearing or bursting during use. Catheters are susceptible to tearing during insertion into or removal from the body of the patient. In addition, the portion of the catheter implanted in the body of the patient can tear at certain locations where the catheter is subjected to localized stress within the body. The extracorporeal portion of an implanted catheter can tear due to mishandling. Catheters also are susceptible to bursting when fluids are injected through the catheter under pressure. Susceptibility to bursting increases when the lumen of the catheter has become occluded at some point along the length of the catheter.

Recently, open-ended cardiovascular access catheters also have been manufactured from polyurethane materials. Polyurethane materials have certain mechanical properties that contrast positively with those of silicone materials. Polyurethane materials have good tensile and tear strength. A catheter constructed from polyurethane material is typically more durable than a similarly sized catheter constructed from silicone material. A catheter constructed from a polyurethane material having a predetermined tensile strength may have a wall thickness that is less than the wall thickness of a catheter constructed from a silicone material having equal tensile strength. Fluid flow rates through a catheter lumen are proportional to the cross-sectional area thereof. The cross-sectional area of catheter lumens can be increased in catheters in which the outer wall thickness can be reduced. A cardiovascular access catheter constructed from a polyurethane material, therefore, can exhibit increased fluid flow rates relative to a similarly sized silicone catheter.

SUMMARY OF THE INVENTION

In one aspect of the present invention the durability and reliability of the performance of long-term cardiovascular access catheters is increased while minimizing injury to patients arising from use thereof.

Another aspect of the invention provides a slit valve in a cardiovascular access catheter that is more durable than known catheters that include such slit valves.

In another aspect of the invention, a slit valve in a cardiovascular access catheter is provided that exhibits improved fluid flow rates relative to known catheters that include such slit valves.

In yet another aspect, the invention provides a slit valve in a cardiovascular access catheter that has a smaller outside diameter than known catheters that include such slit valves.

In one aspect the present invention allows for increased reliance on polyurethane cardiovascular access catheters. Relatedly, another aspect of the invention provides a polyurethane catheter with a closed distal end. In yet another aspect, the invention provides such a catheter with a slit valve that is configured as either a one-way, two-position slit valve or a two-way, three-position slit valve.

Additional aspects and advantages of the invention will be set forth in the description which follows, and in part will be obvious from the description, or may be learned by the practice of the invention. The aspects and advantages of the invention may be realized and obtained by means of the instruments and combinations particularly pointed out in the appended claims.

It has been realized that the opposed slit faces of slit valves in catheters have a tendency to adhere to each other when the opposed slit faces come into abutment with each other in the closed position of the slit valve. According to teachings of the present invention, slit valves in catheters have slit geometries so configured that when pressure differentials are applied between the interior and the exterior of a catheter, the adhesion between abutting slit faces is overcome and broken in an efficient manner. In inventive slit configurations, all or part of each slit is oriented at a non-zero angle relative to the longitudinal axis of the catheter body, and as a result, shear forces and shear stresses are generated at the abutting slit faces of the slit when pressure differentials are applied between the interior and the exterior of that catheter body. In some inventive slit configurations, all or part of the slit partially circumscribes a portion of the outer wall of the catheter body adjacent to and on a first side of the slit. This reduces the restraint on the outward or inward movement of the partially circumscribed outer wall portion imposed by the portion of the outer wall on the opposite side of the slit, when pressure differentials are applied between the interior and the exterior of the body of the catheter.

To achieve the foregoing aspects, and in accordance with the invention as embodied and broadly described herein, a cardiovascular access catheter is provided that has an elongated catheter body enclosing a longitudinally disposed fluid flow lumen and a closed distal end. The catheter body includes an inner surface, an outer surface, and a cylindrical outer wall therebetween of uniform thickness. The catheter body is comprised of a polymeric elastomer material. The cardiovascular access catheter includes a planar slit formed through the outer wall of the catheter body from the outer surface to the inner surface thereof. The slit is contained in a slit orientation plane that intersects the longitudinal axis of the catheter body at a single slit orientation plane longitudinal positioning point and that contains a single unique diameter of the catheter body that intersects the longitudinal axis at the longitudinal positioning point. The slit is so disposed about the longitudinal axis of the catheter body in the slit orientation plane as to be traversed by the unique diameter of the catheter body.

According to one aspect of the invention, the cardiovascular access catheter includes a catheter body comprised of a polyurethane material and a two-way, three-position valve operatively associated therewith. The valve includes the planar slit that separates a first valve wall and a second valve wall that are integrally formed with the outer wall of the catheter body.

The first valve wall terminates in a first slit face that extends from the outer surface to the inner surface of the outer wall of the catheter body between a proximal slit end line and a distal slit end line. The proximal slit end line extends between an outer proximal endpoint on the outer surface of the catheter body and an inner proximal endpoint of the inner surface of the catheter body. The distal slit end line extends between an outer distal endpoint on the outer surface of the catheter body and an inner distal endpoint on the inner surface of the catheter body.

The second valve wall is formed adjacent the first valve wall on the opposite side of the planar slit from the first valve wall. The second valve wall terminates in a second slit face that is opposed to and congruent with the first slit face. The second slit face extends from the outer surface to the inner surface of the outer wall of the catheter body between the proximal slit end line and the distal slit end line.

In the closed position of the valve, the first slit face engages the second slit face in sealing abutment along a slit orientation plane that is disposed at an acute axial deviation angle to the longitudinal axis of the catheter body. The first slit face and the second slit face are so disposed about the longitudinal axis of the catheter body in the slit orientation plane as to be traversed by the unique diameter of the catheter body.

In this configuration, positive and negative pressure differentials created in the lumen relative to the exterior of the catheter body produce a first shear force component in the first valve wall at the first slit face and an oppositely directed second shear force component in the second valve wall at the second slit face. The first shear force component and the second shear force component urge the first slit face and the second slit face out of sealing abutment into oppositely directed translational motion along the slit orientation plane. In this manner, molecular adhesion between the polyurethane material at the first slit face and the polyurethane material at the second slit face is disrupted, allowing the first valve wall and the second valve wall to open inwardly when a negative pressure differential is created or outwardly when a positive pressure differential is created.

An additional catheter embodying teachings of the present invention is constructed from a polymeric elastomer material and includes a valve having a compound slit. According to one aspect of the invention, the compound slit includes a planar slit section that is disposed in a plane containing the longitudinal axis of the catheter body and an additional slit section that adjoins to and is continuous with an end of the planar slit section. A substantial portion of the additional slit section is disposed at an acute axial deviation angle to the longitudinal axis of the catheter body as determined by reference to the angle between the longitudinal axis and a plane tangent to each point on the substantial portion of the additional slit section.

In one aspect of the invention, the compound slit includes a curved slit section and a planar slit section that adjoins to and is continuous with an end of the curved slit section. The curved slit section extends between a proximal endpoint and a distal endpoint that are located on the outer surface of the catheter body so as to avoid defining therebetween on the outer surface a line parallel to the longitudinal axis of the catheter body. The additional slit section can be planar or curved. Alternatively, the additional slit section can include plural planar or curved subsections.

An additional catheter embodying teachings of the present invention is constructed from polymeric elastomer material and includes a valve having a pressure differential sensitized active valve wall member. The active valve wall member is integrally formed with the catheter body and is partially circumscribed by a slit formed through the catheter body. The slit extends between a proximal slit endpoint and a distal slit endpoint located on the outer surface of the catheter body so as to define therebetween a line parallel to the longitudinal axis of the catheter body. The slit reduces the restraint to outward and inward movement of the active valve wall member imposed by adjacent portions of the catheter body. In this configuration, the active valve wall member is facilitated in moving inwardly or outwardly in response to pressure differentials created between the lumen and the exterior of the catheter body.

An additional catheter embodying teachings of the present invention also includes a one-way, two-position infusion valve. The valve includes a planar proximal infusion slit and a planar distal infusion slit formed through the catheter body. The distal infusion slit is located distal from and proximate to the proximal infusion slit.

The proximal infusion slit extends between a first proximal infusion endpoint and a second proximal infusion endpoint disposed on a circumferential proximal infusion arc on the outer surface of the catheter body. The proximal infusion slit is contained in a proximal infusion slit orientation plane that intersects the longitudinal axis of the catheter body at a single slit orientation plane longitudinal positioning point and contains a single unique diameter of the catheter body. The proximal infusion slit is disposed about the longitudinal axis of the catheter body in the proximal infusion slit orientation plane so as to be traversed by a line in the proximal slit infusion orientation plane perpendicular to the unique diameter of the catheter body.

The distal infusion slit extends between a first distal infusion endpoint and a second distal infusion endpoint disposed on a circumferential distal infusion arc on the outer surface of the catheter body distal from the circumferential proximal infusion arc. The distal infusion slit is contained in a distal infusion slit orientation plane that intersects the longitudinal axis of the catheter body at a single slit orientation plane longitudinal positioning point and contains a single unique diameter of the catheter body. The distal infusion slit is disposed about the longitudinal axis of the catheter body in the distal infusion slit orientation plane so as to be traversed by a line in the distal infusion slit orientation plane perpendicular to the unique diameter of the catheter body.

The distal infusion slit orientation plane is disposed at a divergence angle to the proximal infusion slit orientation plane. In this configuration, the longitudinal cross section of the catheter body between the proximal infusion slit and the distal infusion slit assumes a wedge-shaped trapezoidal configuration having the longer of the parallel sides thereof oriented toward the exterior of the catheter body.

The principles of the present invention are applicable to single lumen catheters as well as to catheters that include two or more longitudinally extending fluid flow lumens.

BRIEF DESCRIPTION OF THE DRAWINGS

The manner in which the above-recited and other advantages and aspects of the invention are obtained will be understood by a more particular description of the invention rendered by reference to specific embodiments thereof that are illustrated in the appended drawings. Understanding that these drawings depict only typical embodiments of the invention and are not therefore to be considered limiting of its scope, the invention will be described and explained with additional specificity and detail through the use of the accompanying drawings in which:

FIG. 2 is an enlarged plan view of the distal end of the silicone catheter of FIG. 1 showing a longitudinally extending slit valve of known construction formed in the outer wall thereof;

FIG. 3 is a transverse cross-sectional view of the silicone catheter of FIG. 2 taken along section line 3-3 shown therein illustrating outwardly-directed forces generated by a positive pressure differential;

FIG. 4 is an enlarged detail view of the portion of the cross section of FIG. 3 depicting the slit valve of known construction, illustrating a circumferential tangential tensile stress;

FIG. 5 is a transverse cross-sectional view like that of FIG. 3 showing the valve in an outwardly open position;

FIG. 6 is a transverse cross-sectional view like that of FIG. 3 illustrating inwardly-directed forces generated by a negative pressure differential;

FIG. 7 is an enlarged detail view of the portion of the cross section of FIG. 6 depicting the slit valve of known construction illustrating a circumferential tangential compressive stress;

FIG. 8 is a transverse cross-sectional view like that of FIG. 3 showing the valve in an inwardly open position;

DETAILED DESCRIPTION OF THE INVENTION

Figure 1:
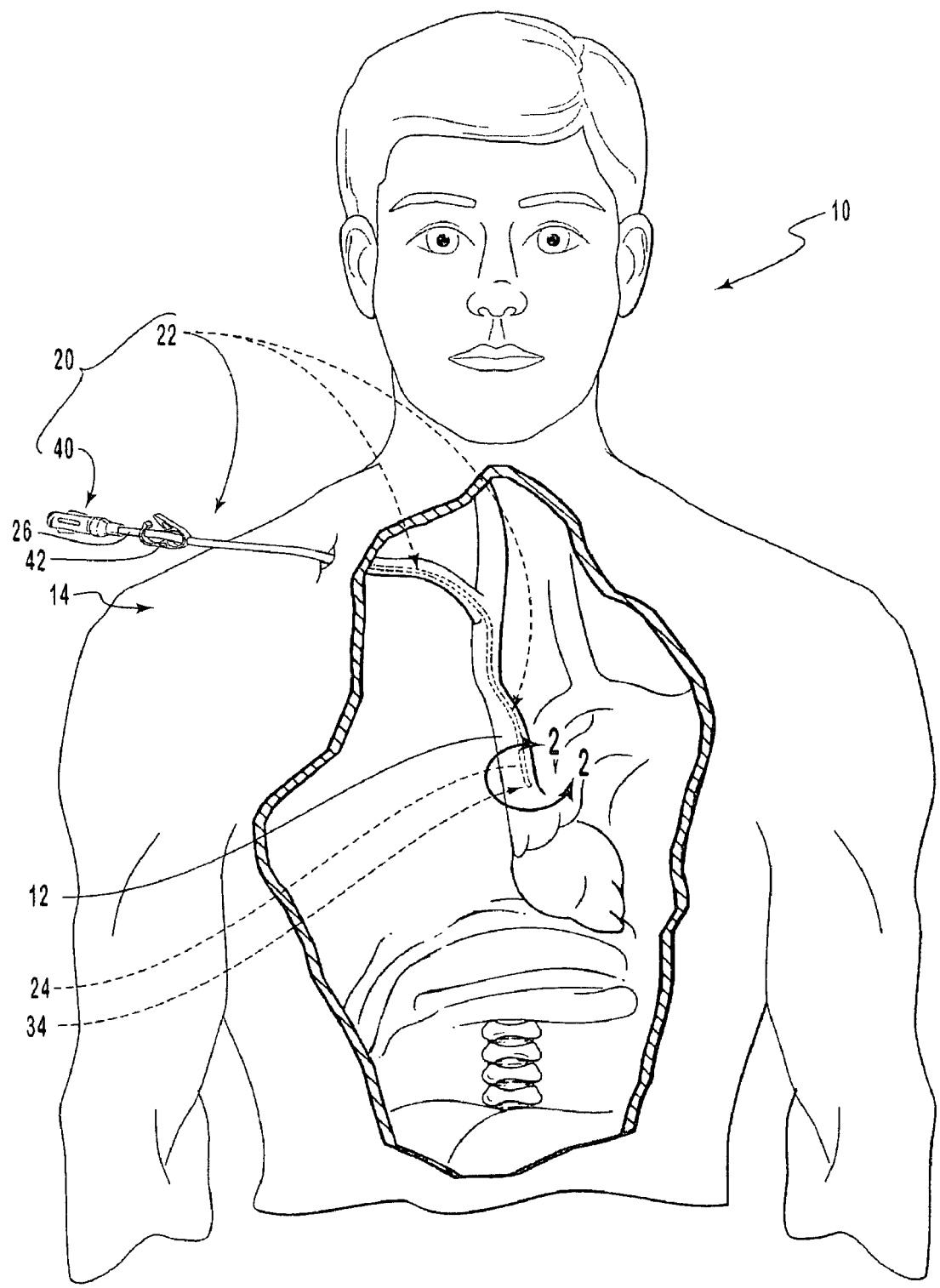
FIG. 1 is a perspective view of a first cardiovascular access system implanted in the body of a patient so as to afford direct external access by medical personnel through the proximal end of a known, valved silicon catheter that is used in the system.

It has been realized that the opposed slit faces of slit valves in silicone and polyurethane tubing have a tendency to adhere to each other when the opposed slit faces come into abutment with each other in the closed position of the slit valve. According to teachings of the present invention, slit valves in catheters have slit geometries so configured that when pressure differentials are applied between the interior and the exterior of a catheter, the adhesion between abutting slit faces is overcome and broken in an efficient manner. In inventive slit configurations, all or part of each slit is oriented at a non-zero angle relative to the longitudinal axis of the catheter body, and as a result, shear forces and shear stresses are generated at the abutting slit faces of the slit when pressure differentials are applied between the interior and the exterior of the catheter body.

Stress arises in the outer wall of a closed cylindrical structure when pressure differentials are created between the interior and the exterior of the structure. The stress is characterizable in terms of magnitude and orientation in relation to the geometry of the cylinder by resolving the stress into mutually orthogonal components, such as a tangential stress $\sigma_T$ component, a radial stress $\sigma_R$ component, and a longitudinal stress $\sigma_L$ component. If the slit faces of a slit valve formed in the outer wall of a catheter have adhered, and pressure differentials are created between the interior and the exterior of the catheter body, the catheter body can be treated as a closed cylindrical pressure vessel. Known equations for tangential stress $\sigma_T$, radial stress $\sigma_R$, and longitudinal stress $\sigma_L$ in cylindrical pressure vessels can then be used to characterize the stress in the outer wall of the catheter body. While these known equations were derived originally in relation to pressure vessels that are rigid, the known equations still provide useful general information regarding the nature of the stress produced in the outer wall of a flexible catheter body by the creation of a pressure differential between the interior and the exterior of that catheter body.

By way of establishing a necessary convention in the use of such known equations, the pressure differential between the interior and the exterior of a catheter body will be equal to the pressure outside the catheter body subtracted from the pressure inside the catheter body. Thus, $$\text{Pressure Differential } p_\Delta = (p_i - p_o), \text{ where} \quad \text{Equation No. 1}$$

$p_i$ pressure inside catheter body, and
$p_o$ pressure outside catheter body.

A positive pressure differential $p_\Delta$ exists when the pressure $p_i$ inside the catheter body is greater than the pressure $p_o$ outside the catheter body. A negative pressure differential $p_\Delta$ exists when the pressure $p_i$ inside the catheter body is less than the pressure $p_o$ outside the catheter body.

In this manner, the stress produced at any location within a cylindrical catheter body at a distance R from the longitudinal axis thereof by a pressure differential $p_\Delta$ between the interior and the exterior of the catheter body can be characterized using the following equations in which positive values for stress indicate tensile stress, and negative values for stress indicate compressive stress.

$$\text{Tangential Stress } \sigma_T = \frac{r_i^2 p_\Delta}{r_o^2 - r_i^2}\left(1 + \frac{r_o^2}{R^2}\right), \text{ where} \quad \text{Equation No. 2}$$

R=radial distance from longitudinal axis of catheter body
$r_i$=inside radius of pressurized catheter body
$r_o$=outside radius of pressurized catheter body
$p_\Delta$=pressure differential.

$$\text{Radial Stress } \sigma_R = \frac{r_i^2 p_\Delta}{r_o^2 - r_i^2}\left(1 - \frac{r_o^2}{R^2}\right) \quad \text{Equation No. 3}$$

$$\text{Longitudinal Stress } \sigma_L = \frac{p_\Delta r_i^2}{r_o^2 - r_i^2} \quad \text{Equation No. 4}$$

Equation Nos. 1-4 are useful for determining whether the tangential stress $\sigma_T$, radial stress $\sigma_R$, and longitudinal stress $\sigma_L$ resolved components of the stress in the outer wall of a catheter body are positive or negative, and therefore whether those stress components are compressive or tensile in nature, respectively. If a positive pressure differential $p_\Delta$ exists between the interior and the exterior of the catheter body, Equation Nos. 2-4 indicate that tangential stress $\sigma_T$ and longitudinal stress $\sigma_L$ are tensile, while radial stress $\sigma_R$ is compressive. If a negative pressure differential $p_\Delta$ exists between the interior and the exterior of the catheter body, Equation Nos. 2-4 indicate that tangential stress $\sigma_T$ and longitudinal stress $\sigma_L$ are compressive, while radial stress $\sigma_R$ is tensile. The stress arising in the outer wall of a catheter body when a pressure differential is created between the interior and the exterior of the catheter body will be discussed in relation to embodiments of slit valves disclosed herein that incorporate teachings of the present invention.

FIGS. 9-14 depict a cardiovascular access catheter device 80 that embodies teachings of the present invention.

Figure 9:
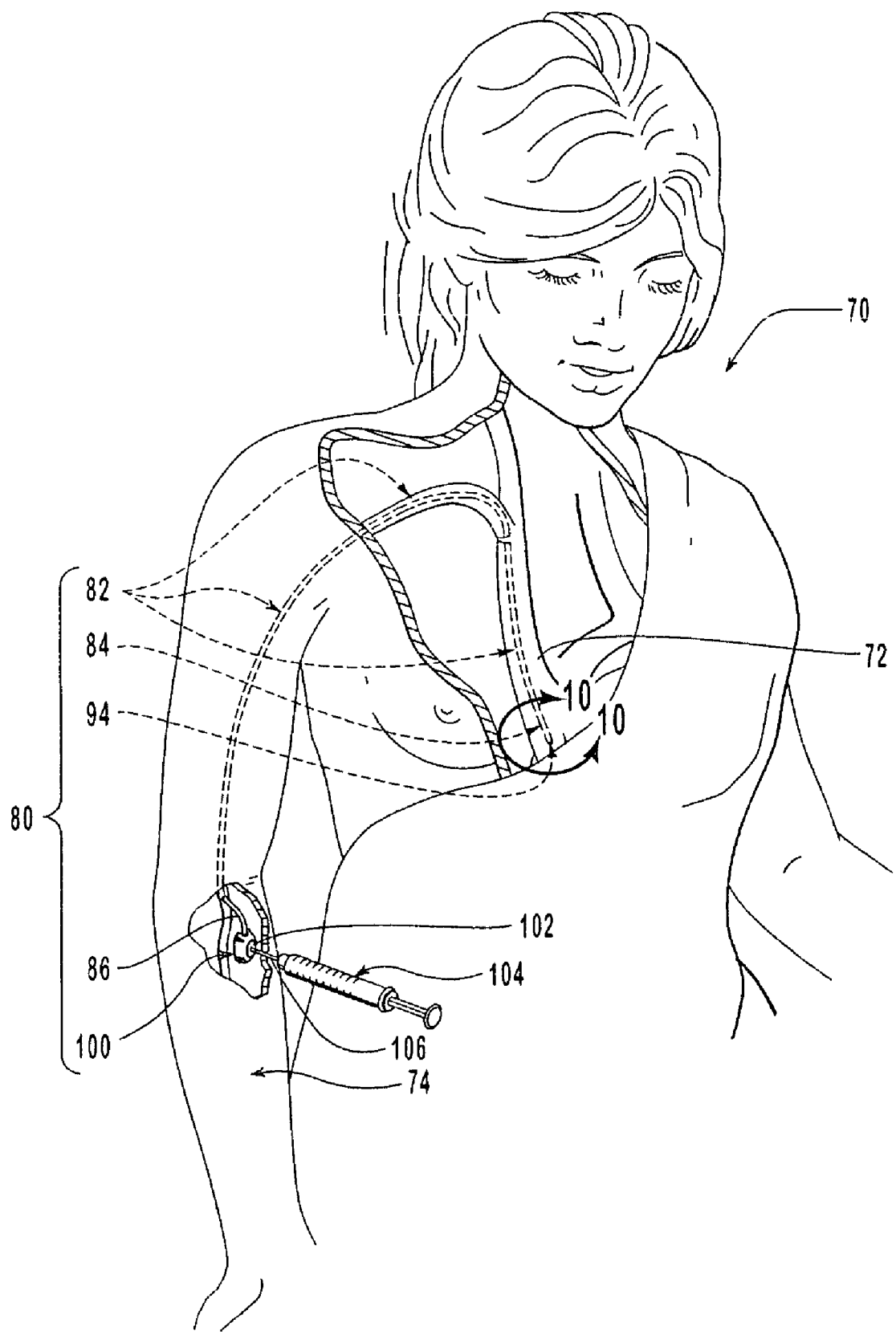
FIG. 9 is a perspective view of a second cardiovascular access system implanted in the body of a patient so as to afford transcutaneous access with a hypodermic syringe to an implanted single reservoir port coupled to the proximal end of a single lumen polymeric elastomer catheter incorporating teachings of the present invention.

FIG. 9 is a perspective view of cardiovascular access catheter device 80 implanted in the body of a patient 70 for whom a therapeutic procedure is to be undertaken on an intermittent basis, by way of example, in the superior vena cava 72 of the venous subsystem of the cardiovascular system. Catheter device 80 includes a soft, flexible, elongated catheter body 82 comprised of a polymeric elastomer material. Broadly, the polymeric elastomer material has a flexural modulus less than about 30,000 psi (207 MPa). More narrowly, the polymeric elastomer material has a flexural modulus in a range from approximately 250 psi (1.72 MPa) to approximately 20,000 psi (138 MPa). Most narrowly, the polymeric elastomer material has a flexural modulus in a range from approximately 500 psi (3.45 MPa) to approximately 15,000 psi (103 MPa).

For example, the polymeric elastomer material can be a polyurethane material, a silicone material, or a copolymer material. An exemplary polyurethane elastomer material that can be used to construct catheter body 82 is sold under the trade name TECOFLEX® by Thermedics Polymer Products of Wilmington, Mass. The polyurethane elastomer material has a durometer in a range from approximately 70 Shore A to approximately 100 Shore A. An exemplary silicone elastomer material that can be used to construct catheter body 82 is sold under the trade name SILASTIC® by Dow Corning Corporation of Midland, Mich. The silicone elastomer material has a durometer in a range from approximately 35 Shore A to approximately 60 Shore A.

Catheter body 82 has a distal portion 84 that is intended to reside in superior vena cava 72 and a proximal end 86 that is attached to a subcutaneously implantable access port 100. The entire length of catheter body 82 and access port 100 are implanted within the body of patient 70. A significant portion of catheter body 82 proximate distal portion 84 resides in the contiguous blood vessels extending away from superior vena cava 72 and into right arm 74 of the body of patient 70. In right arm 74, a section of catheter body 82 extends through an incision in the wall of a blood vessel into the surrounding subcutaneous soft tissue, in which access port 100 resides. Sutures may be used to secure access port 100 to the soft tissue.

Access port 100 includes a needle-penetrable septum 102, which is comprised of a silicone material. A hypodermic syringe 104 with a needle 106 is used with catheter device 80 to infuse fluids into or aspirate fluids from the body of patient 70. To infuse or aspirate fluids, needle 106 of syringe 104 is inserted through the skin and tissue of right arm 74 and into access port 100 through needle-penetrable septum 102. The syringe plunger is depressed, and fluids contained therein travel from syringe 104 through needle 106 into access port 100 and catheter body 82. The fluids exit catheter body 82 at distal portion 84 and enter superior vena cava 72 at the intended site of therapeutic treatment.

Alternatively, proximal end 86 of catheter body 82 could reside outside the body of patient 70 in the manner illustrated in FIG. 1 and discussed previously herein. In such a case, proximal end 86 could include a luer connector for providing a connection between catheter device 80 and a syringe or other medical equipment.

Figure 10:
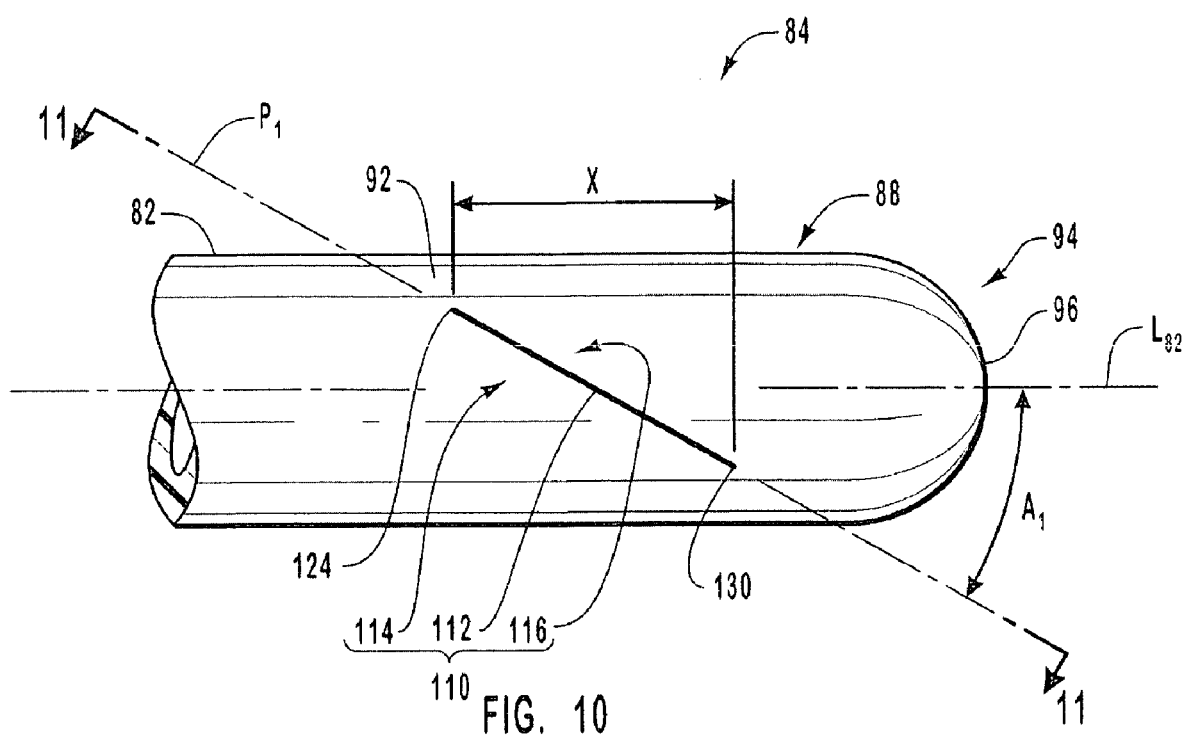
FIG. 10 is an enlarged plan view of the distal end of the catheter of FIG. 9 showing a first embodiment of a slit valve incorporating teachings of the present invention formed in the outer wall thereof and contained in a slit orientation plane disposed at an acute axial deviation angle to the longitudinal axis of the body of the catheter.

FIG. 10 is an enlarged plan view of distal portion 84 of catheter body 82 shown in FIG. 9 showing a first embodiment of a slit valve incorporating teachings of the present invention. Catheter body 82 is seen to have a longitudinal axis $L_{82}$ and to terminate in a closed distal tip 94. Distal portion 84 of catheter body 82 includes a cylindrical circumferential outer wall 88 and a semispherical terminal endwall 96 that is continuous with outer wall 88. A slit valve 110 is formed through outer wall 88 in distal portion 84 of catheter body 82.

Slit valve 110 includes a planar slit 112 that is disposed in a slit orientation plane $P_1$ shown on edge in FIG. 10. Planar slit 112 extends longitudinally through outer wall 88 at an acute axial deviation angle $A_1$ relative to longitudinal axis $L_{82}$ of catheter body 82. Broadly, acute axial deviation angle $A_1$ can be in a range from about 10° to about 80°. More narrowly, acute axial deviation angle $A_1$ can be in a range from about 20° to about 70°. Most narrowly, acute axial deviation angle $A_1$ can be in a range from about 30° to about 60°. The optimum angle for acute axial deviation angle $A_1$ might be at least partially a function of the material from which outer wall 88 is constructed. If the material from which outer wall 88 is constructed is semicrystalline, the optimum angle for acute axial deviation angle $A_1$ might be at least partially a function of the degree of crystallinity.

Planar slit 112 extends on an outer surface 92 of catheter body 82 between an outer proximal endpoint 124 and an outer distal endpoint 130, which have a longitudinal separation X in a direction parallel to longitudinal axis $L_{82}$ of catheter body 82. Planar slit 112 separates a first valve wall 114 and a second valve wall 116 that are otherwise integrally formed with outer wall 88 of catheter body 82.

Figure 11:
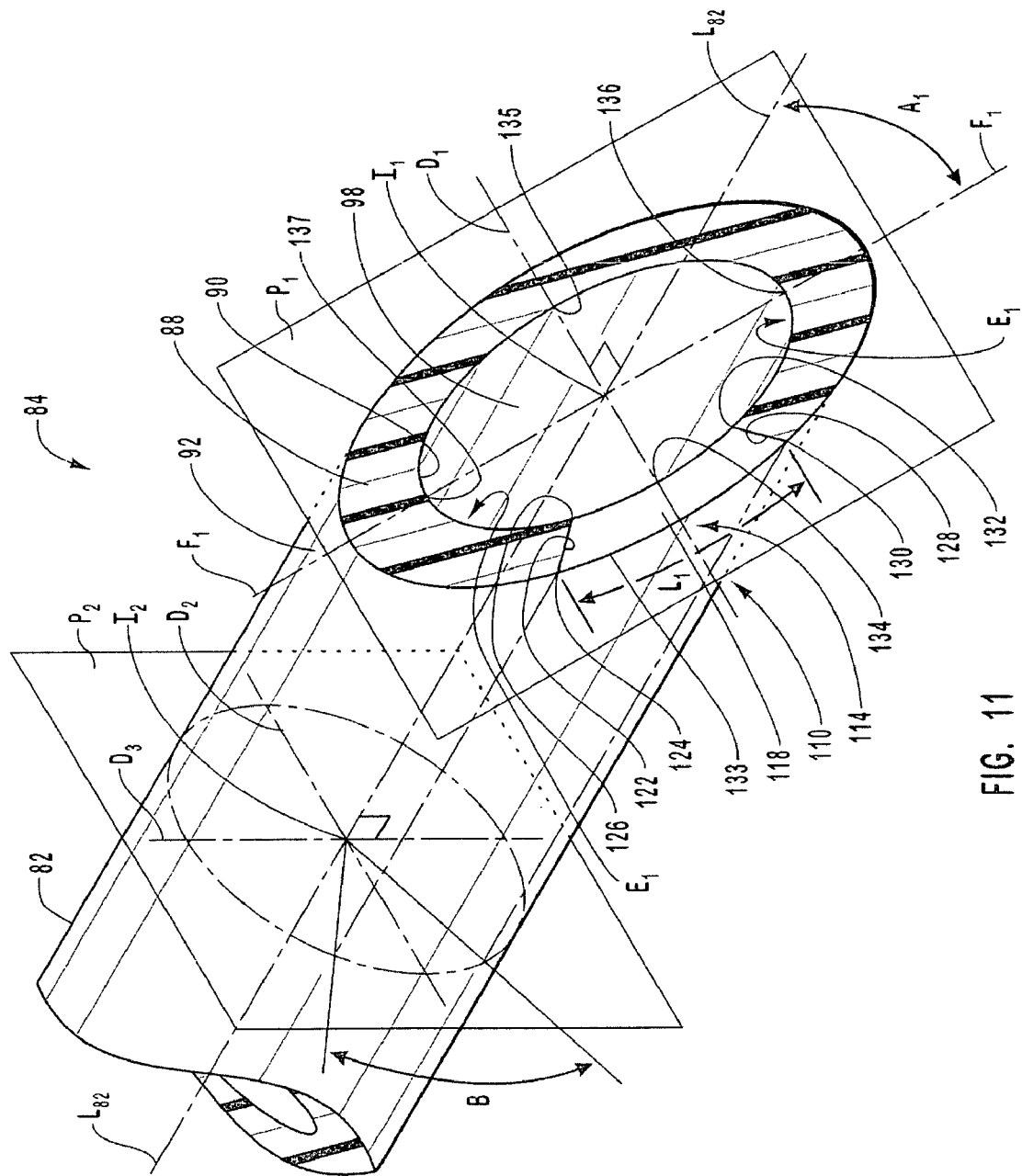
FIG. 11 is an enlarged perspective view of the portion of the catheter of FIG. 10 located proximal of the slit orientation plane in which the slit valve of FIG. 10 is contained.

FIG. 11 is an enlarged perspective view of the section of distal portion 84 of FIG. 10 located proximal of slit orientation plane $P_1$ in which slit valve 110 is contained. As seen in FIG. 11, outer wall 88 extends between outer surface 92 and inner surface 90 of catheter body 82 and has a uniform thickness therebetween. Catheter body 82 encloses a longitudinally disposed fluid flow lumen 98. Alternatively, catheter body 82 could enclose two or more fluid flow lumens.

Planar slit 112 of slit valve 114 extends radially through catheter body 82 from outer surface 92 to inner surface 90 and longitudinally between a proximal slit end line 122 and a distal slit end line 128. Proximal slit end line 122 extends through catheter body 82 between outer proximal endpoint 124 on outer surface 92 and inner proximal endpoint 126 on inner surface 90 of catheter body 82. Similarly, distal slit end line 128 extends through catheter body 82 between outer distal endpoint 130 on outer surface 92 and inner distal endpoint 132 on inner surface 90 of catheter body 82. First valve wall 114 terminates at planar slit 112 in a first slit face 118 shown in FIG. 11. Although not shown in FIG. 11, second valve wall 116 terminates in a second slit face 120 that is congruent with first slit face 118.

A slit curve 133 extends along outer surface 92 of catheter body 82 between outer proximal endpoint 124 and outer distal endpoint 130. Outer proximal endpoint 124 and outer distal endpoint 130 are separated angularly about longitudinal axis $L_{82}$ from one another by an angular separation B, which is illustrated in FIG. 11 in a plane $P_2$ that is oriented perpendicular to longitudinal axis $L_{82}$ of catheter body 82. Broadly, outer proximal endpoint 124 and outer distal endpoint 130 may have an angular separation B in a range from about 5° to about 135°. More narrowly, outer proximal endpoint 124 and outer distal endpoint 130 may have an angular separation B in a range from about 15° to about 125°. Most narrowly, outer proximal endpoint 124 and outer distal endpoint 130 may have an angular separation B in a range from about 25° to about 115°.

In this configuration, outer proximal endpoint 124 and outer distal endpoint 130 are so located on outer surface 92 of catheter body 82 as to avoid defining therebetween on outer surface 92 a line parallel to longitudinal axis $L_{82}$ of catheter body 82. In addition, because outer proximal endpoint 124 and outer distal endpoint 130 are separated longitudinally by longitudinal separation X as shown in FIG. 10, outer proximal endpoint 124 and outer distal endpoint 130 are so located on outer surface 92 of catheter body 82 as to avoid defining therebetween on outer surface 92 an arc in a plane perpendicular to longitudinal axis $L_{82}$ of catheter body 82. Plane $P_2$ exemplifies a plane perpendicular to longitudinal axis $L_{82}$ of catheter body 82.

As shown in FIG. 11, slit orientation plane $P_1$ intersects longitudinal axis $L_{82}$ of catheter body 82 at a single slit orientation plane longitudinal positioning point $I_1$ that serves to define the longitudinal position along catheter body 82 of slit orientation plane $P_1$. Due to the inclination of slit orientation plane $P_1$ at axial deviation angle $A_1$ relative to longitudinal axis $L_{82}$, a unique diameter $D_1$ of catheter body 82 both passes through longitudinal positioning point $I_1$ and is contained in slit orientation plane $P_1$. In contrast, plane $P_2$, which is perpendicular to longitudinal axis $L_{82}$, intersects longitudinal axis $L_{82}$ at a longitudinal positioning point $I_2$ and contains a plurality of diameters of catheter body 82, including diameters $D_2$ and $D_3$. Planar slit 112 is so disposed about longitudinal axis $L_{82}$ of catheter body 82 in slit orientation plane $P_1$ as to be traversed by unique diameter $D_1$ of catheter body 82.

Planar slit 112 has a slit length $L_1$ that is measured along slit curve 133 between outer proximal endpoint 124 and outer distal endpoint 130.

Figure 12:
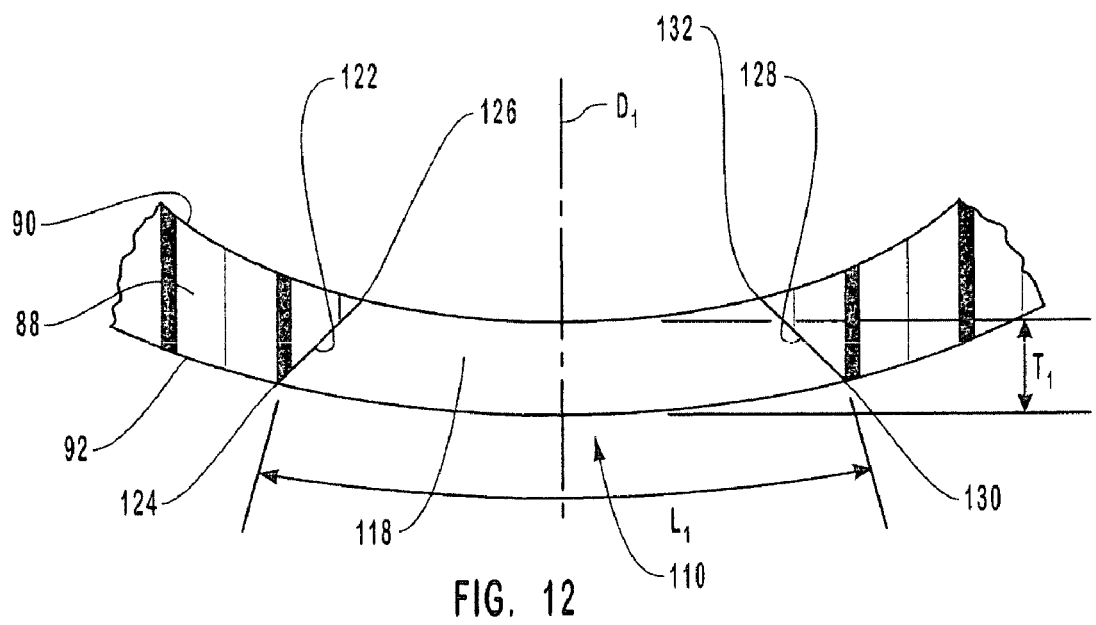
FIG. 12 is an enlarged view of the face of the slit valve shown in FIG. 11.

FIG. 12 is an enlarged view of first slit face 118 of slit valve 110 shown in FIG. 11. Outer wall 88 of catheter body 82 has a uniform thickness $T_1$ between outer surface 92 and inner surface 90 of catheter body 82. Uniform thickness $T_1$ is measured along any diameter of catheter body 82, such as unique diameter $D_1$ shown in FIG. 12. Broadly, slit length $L_1$ can be in a range from about 1 to about 10 times thickness $T_1$ of outer wall 88 of catheter body 82. More narrowly, slit length $L_1$ can be in a range from about 2 to about 7.5 times thickness $T_1$ of outer wall 88 of catheter body 82. Most narrowly, slit length $L_1$ can be in a range from about 3 to about 5 times thickness $T_1$ of outer wall 88 of catheter body 82. Broadly, the longitudinal separation X shown in FIG. 10 between outer proximal endpoint 124 and outer distal endpoint 130 can be in a range from about 1 to about 10 times thickness $T_1$ of outer wall 88 of catheter body 82. More narrowly, longitudinal separation X can be in a range from 2 to about 7.5 times thickness $T_1$ of outer wall 88 of catheter body 82. Most narrowly, longitudinal separation X can be in a range from about 3 to about 5 times thickness $T_1$ of outer wall 88 of catheter body 82.

It has been realized that the opposed slit faces of slit valves in silicone and polyurethane catheters have a tendency to adhere together when the slit valve is in the closed position. This adhering of the slit faces prevents the slit valve from opening properly and renders the slit valve inoperable. The adhesion is attributed to intermolecular chemical bonding, intermolecular forces, and intermolecular entanglement between molecules in material at one slit face of a slit valve and molecules in material at the opposing slit face of the slit valve.

Orienting planar slit 112 of slit valve 110 at an acute axial deviation angle $A_1$ relative to longitudinal axis $L_{82}$ of catheter body 82 contributes to overcoming adhesion between first slit face 118 and second slit face 120. In this configuration, shear forces and resulting stresses are generated at the abutting first slit face 118 and second slit face 120 when a tangential tensile stress $\sigma_{Tt}$ or a tangential compressive stress $\sigma_{Tc}$ is generated in outer wall 88 of catheter body 82 due to pressure differentials between lumen 98 and the exterior of catheter body 82. Therefore, any molecules at first slit face 118 that are bonded to, attracted to, or entangled with molecules at slit face 120 of slit valve 110 will be subjected to shear forces. Shear forces contribute to breaking chemical bonds and freeing entangled molecules, thereby allowing slit valve 110 to open properly.

Figure 13A:
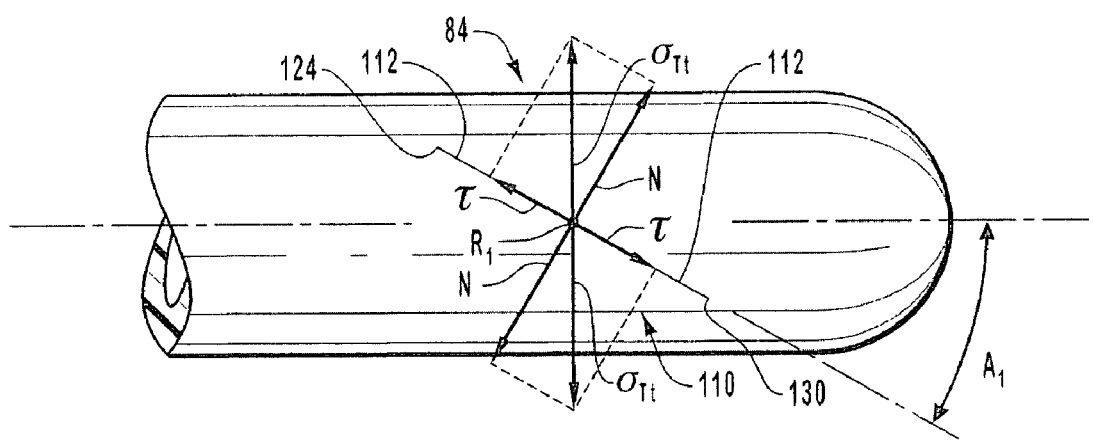
FIG. 13A is the slit valve of FIG. 10 enhanced diagrammatically to depict components of stresses arising in the outer wall of the illustrated catheter when a positive pressure differential is created in the catheter relative to the exterior thereof.

FIG. 13A shows slit valve 110 of FIG. 10 enhanced diagrammatically to depict resolved components of a tangential tensile stress $\sigma_{Tt}$ generated in outer wall 88 of catheter body 82 when a positive pressure differential is created in lumen 98 relative to the exterior of catheter body 82. Tangential tensile stress $\sigma_{Tt}$ is characterized by Equation No. 2 above. At any point in outer wall 88 of catheter body 82, tangential tensile stress $\sigma_{Tt}$ is resolvable into normal stress components and shear stress components relative to planar slit 112. These resolved stress components are shown by way of illustration at an idealized point $R_1$ of minimal extent traversed by planar slit 112. If first slit face 118 and second slit face 120 are adhered, tangential tensile stress $\sigma_{Tt}$ is resolvable at point $R_1$ into a normal stress component N that acts perpendicular to planar slit 112, and a shear stress component $\tau$ that acts parallel to planar slit 112.

Figure 13B:
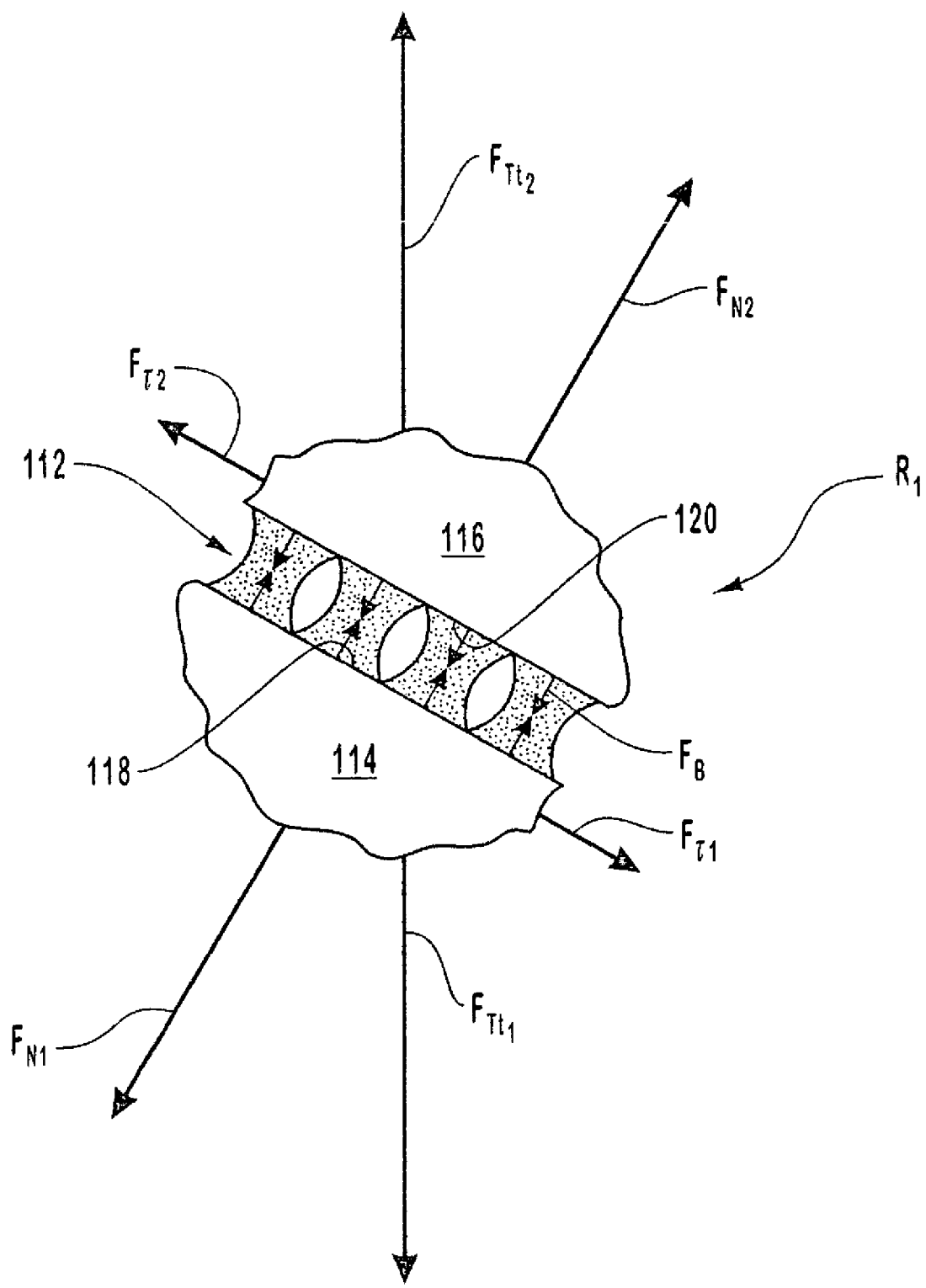
FIG. 13B is an enlarged detail view of a portion of the slit valve of FIG. 13A enhanced diagrammatically to depict components of forces acting on the outer wall of the illustrated catheter at a selected point $R_1$.

FIG. 13B is an enlarged view of point $R_1$ of FIG. 13A. As seen therein, first slit face 118 and second slit face 120 are constrained to remain in contact by adhesion forces $F_B$, which are generated by intermolecular chemical bonding, intermolecular forces, and intermolecular entanglement between molecules in material at first slit face 118 of slit valve 110 and molecules in material at slit face 120 of slit valve 110. As stress is defined as force per unit area, the sum of the forces acting on any finite portion of outer wall 88 of catheter body 82 of known dimensions can be determined. Assuming that point $R_1$ shown in FIG. 13B represents a small, but finite portion of outer wall 88 of catheter body 82 traversed by planar slit 112 having known dimensions, the sum of the forces acting on point $R_1$ can be determined from the tangential tensile stress $\sigma_{Tt}$. As shown in FIG. 13B, a first tangential tensile force $F_{Tt1}$ acts on the portion of first valve wall 114 contained in point $R_1$, and an equal and oppositely directed second tangential tensile force $F_{Tt2}$ acts on the portion of second valve wall 116 contained in point $R_1$.

First tangential tensile force $F_{Tt1}$ and second tangential tensile force $F_{Tt2}$ shown in FIG. 13B are resolvable into normal and shear components thereof relative to planar slit 112 in the same manner as tangential tensile stress $\sigma_{Tt}$, which was described previously in relation to FIG. 13A. In this manner, first tangential tensile force $F_{Tt1}$ is resolved into a first normal force $F_{N1}$ that acts on the portion of first valve wall 114 contained in point $R_1$ in a direction normal or perpendicular to planar slit 112, and a first shear force $F_{\tau 1}$ that acts on the portion of first valve wall 114 contained in point $R_1$ in a direction parallel to planar slit 112. Second tangential tensile force $F_{Tt2}$ is resolved into a second normal force $F_{N2}$ that acts on the portion of second valve wall 116 contained in point $R_1$ in a direction normal or perpendicular to planar slit 112, and a second shear force $F_{\tau 2}$ that acts on the portion of second valve wall 116 contained in point $R_1$ in a direction parallel to planar slit 112. First normal force $F_{N1}$ is equal in magnitude and oppositely directed relative to second normal force $F_{N2}$, and first shear force $F_{\tau 1}$ is equal in magnitude and oppositely directed relative to second shear force $F_{\tau 2}$.

First shear force $F_{\tau 1}$ urges first slit face 118 in a first direction parallel to planar slit 112, while second shear force $F_{\tau 2}$ urges second slit face 120 in an opposite direction to produce a shearing action between first slit face 118 and second slit face 120. This shearing action generated by first shear force $F_{\tau 1}$ and second shear force $F_{\tau 2}$ contributes to disrupting adhesion forces $F_B$, which are generated by intermolecular chemical bonding, intermolecular forces, and intermolecular entanglement between molecules in material at first slit face 118 of slit valve 110 and molecules in material at slit face 120 of slit valve 110. In this manner, first slit face 118 and second slit face 120 are urged out of sealing abutment into oppositely directed translational motion along slit orientation plane $P_1$ by first shear force $F_{\tau 1}$ and second shear force $F_{\tau 2}$. While this translational motion is so minimal as to be theoretical, it is significant on a molecular scale. This shearing process illustrated in FIG. 13B enables first valve wall 114 and second valve wall 116 to open outwardly in response to forces acting on outer wall 88 of catheter body 82 generated by a positive pressure differential created between lumen 98 and the exterior of catheter body 82.

Figure 14A:
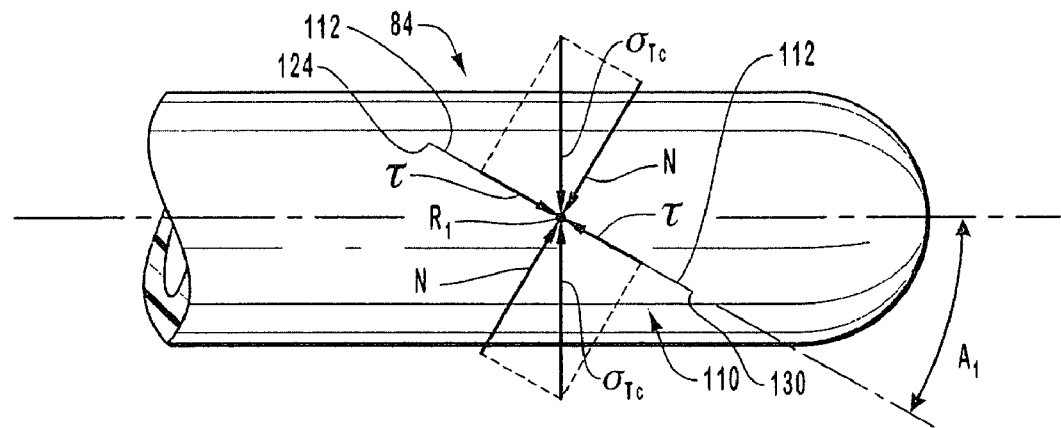
FIG. 14A is the slit valve of FIG. 10 enhanced diagrammatically to depict components of the stresses arising in the outer wall of the illustrated catheter when a negative pressure differential is created in the catheter relative to the exterior thereof.

FIG. 14A shows slit valve 110 of FIG. 10 enhanced diagrammatically to depict resolved components of a tangential compressive stress $\sigma_{Tc}$ generated in outer wall 88 of catheter body 82 when a negative pressure differential is created in lumen 98 relative to the exterior of catheter body 82. Tangential compressive stress $\sigma_{Tc}$ is characterized by Equation No. 2 above. At any point in outer wall 88 of catheter body 82, tangential compressive stress $\sigma_{Tc}$ is resolvable into normal stress components and shear stress components relative to planar slit 112. These resolved stress components are shown by way of illustration at an idealized point $R_1$ of minimal extent traversed by planar slit 112. If first slit face 118 and second slit face 120 are adhered, tangential compressive stress $\sigma_{Tc}$ is resolvable at point $R_1$ into a normal stress component N acting normal to planar slit 112 and a shear stress component $\tau$ acting parallel to planar slit 112 in the same manner described above in relation to FIG. 13A.

Figure 14B:
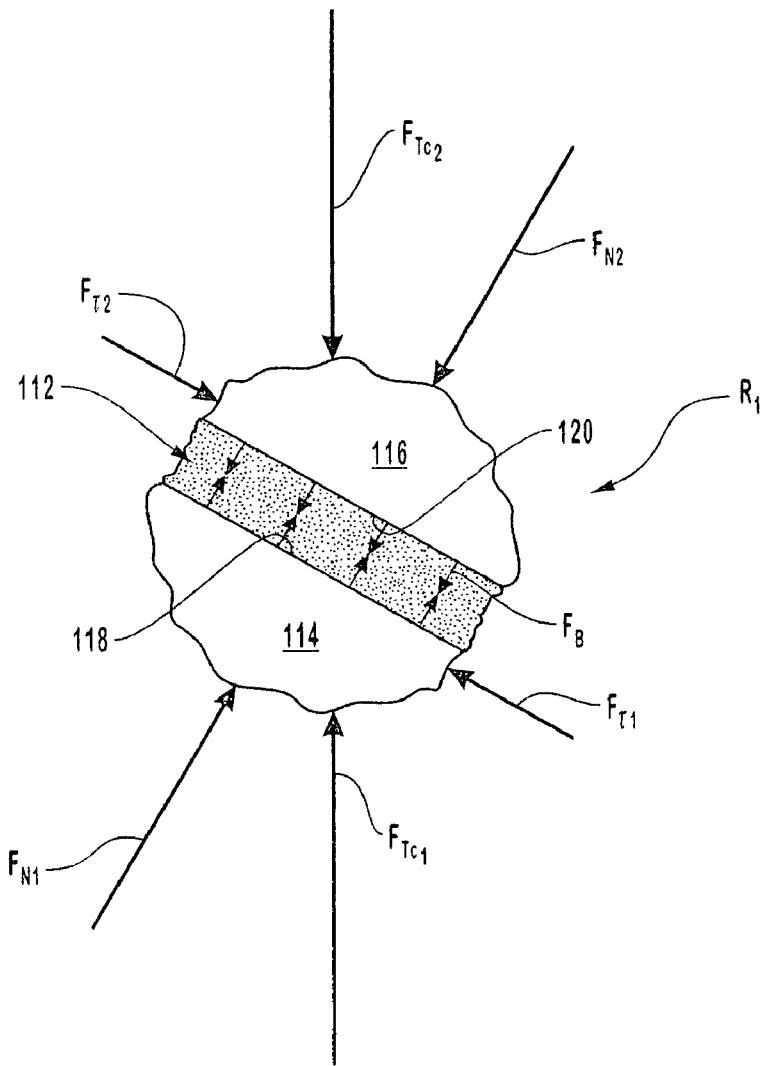
FIG. 14B is an enlarged detail view of a portion of the slit valve of FIG. 14A enhanced diagrammatically to depict components of forces acting on the outer wall of the illustrated catheter at a selected point $R_1$.

FIG. 14B is an enlarged view of point $R_1$ of FIG. 14A. As seen therein, first slit face 118 and second slit face 120 are adhered and constrained to remain in contact by adhesion forces $F_B$, which are generated by intermolecular chemical bonding, intermolecular forces, and intermolecular entanglement between molecules in material at first slit face 118 of slit valve 110 and molecules in material at slit face 120 of slit valve 110. As stress is defined as force per unit area, the sum of the forces acting on any finite portion of outer wall 88 of catheter body 82 of known dimensions can be determined. Assuming that point $R_1$ shown in FIG. 14B represents a small, but finite portion of outer wall 88 of catheter body 82 traversed by planar slit 112 having known dimensions, the sum of the forces acting on point $R_1$ can be determined from the tangential compressive stress $\sigma_{Tc}$. As shown in FIG. 14B, a first tangential compressive force $F_{Tc1}$ acts on the portion of first valve wall 114 contained in point $R_1$, and an equal and oppositely directed second tangential compressive force $F_{Tc2}$ acts on the portion of second valve wall 116 contained in point $R_1$.

First tangential compressive force $F_{Tc1}$ and second tangential compressive force $F_{Tc2}$ shown in FIG. 14B are resolvable into normal and shear components relative to planar slit 112 in the same manner as tangential compressive stress $\sigma_{Tc}$, which was described previously in relation to FIG. 14A. In this manner, first tangential compressive force $F_{Tc1}$ is resolved into a first normal force $F_{N1}$ that acts on the portion of first valve wall 114 contained in point $R_1$ in a direction normal or perpendicular to planar slit 112, and a first shear force $F_{\tau 1}$ that acts on the portion of first valve wall 114 contained in point $R_1$ in a direction parallel to planar slit 112. Second tangential compressive force $F_{Tc2}$ is resolved into a second normal force $F_{N2}$ that acts on the portion of second valve wall 116 contained in point $R_1$ in a direction normal or perpendicular to planar slit 112, and a second shear force $F_{\tau 2}$ that acts on the portion of second valve wall 116 contained in point $R_1$ in a direction parallel to planar slit 112. First normal force $F_{N1}$ is equal in magnitude and oppositely directed relative to second normal force $F_{N2}$, and first shear force $F_{\tau 1}$ is equal in magnitude and oppositely directed relative to second shear force $F_{\tau 2}$.

First shear force $F_{\tau 1}$ and second shear force $F_{\tau 2}$ shown in FIG. 14B contribute to overcoming adhesion between first slit face 118 and second slit face 120 in the same manner as that described above in relation to FIG. 13B. First shear force $F_{\tau 1}$ urges first slit face 118 in a first direction parallel to planar slit 112, while second shear force $F_{\tau 2}$ urges second slit face 120 in an opposite direction to produce a shearing action between first slit face 118 and second slit face 120. This shearing action generated by first shear force $F_{\tau 1}$ and second shear force $F_{\tau 2}$ contributes to disrupting adhesion forces $F_B$, which are generated by intermolecular chemical bonding, intermolecular forces, and intermolecular entanglement between molecules in material at first slit face 118 of slit valve 110 and molecules in material at slit face 120 of slit valve 110. In this manner, first slit face 118 and second slit face 120 are urged out of sealing abutment into oppositely directed translational motion along slit orientation plane $P_1$ by first shear force $F_{\tau 1}$ and second shear force $F_{\tau 2}$. While this translational motion is so minimal as to be theoretical, it is significant on a molecular scale. This shearing process illustrated in FIG. 14B enables first valve wall 114 and second valve wall 116 to open inwardly in response to forces acting on outer wall 88 of catheter body 82 generated by a negative pressure differential created between lumen 98 and the exterior of catheter body 82.

By referring to the location of first slit face 118 in FIG. 11, it can be seen that the planar slit 112 shown in FIG. 10 is so disposed about longitudinal axis $L_{82}$ of catheter body 82 in slit orientation plane $P_1$ as to be traversed by unique diameter $D_1$ of catheter body 82. Unique diameter $D_1$ of catheter body 82 intersects the interior of outer wall 88 of catheter body 82 at a first point 134 along slit valve 110 and at a second point 135 that is diametrically opposite from first point 134 on inner surface 90 of outer wall 88 of catheter body 82. At points like first point 134 and second point 135 located on unique diameter $D_1$, the magnitude of shear forces that arise in outer wall 88 of catheter body 82 due to tangential stress $\sigma_T$ is a maximum.

On the other hand, a unique line $F_1$ is both contained in slit orientation plane $P_1$ and perpendicular to unique diameter $D_1$ at longitudinal positioning point $I_1$. Unique line $F_1$ is coincident with the major axis of the ellipse $E_1$ formed by the intersection of inner surface 90 of outer wall 88 of catheter body 82 with slit orientation plane $P_1$, while unique diameter $D_1$ is coincident with the minor axis of ellipse $E_1$. Unique line $F_1$ intersects inner surface 90 of outer wall 88 of catheter body 82 at a third point 136 and at a fourth point 137 that is diametrically opposite from third point 136 on inner surface 90 of outer wall 88 of catheter body 82. At points like third point 136 and fourth point 137 located on unique line $F_1$, the magnitude of shear forces that arise in outer wall 88 of catheter body 82 due to tangential stress $\sigma_T$ is a minimum. As the location of slit valve 110 is moved in slit orientation plane $P_1$ circumferentially in either direction about longitudinal positioning point $I_1$ from first point 134, the magnitude of the oppositely directed shear forces acting on first slit face 118 and second slit face 120 due to tangential stress $\sigma_T$ decreases to a minimum at third point 136 and fourth point 137.

Longitudinal stress $\sigma_L$ generated in outer wall 88 of catheter body 82 due to a pressure differential created between lumen 98 and the exterior of catheter body 82 is characterized by Equation No. 4 above. Due to the inclination of slit orientation plane $P_1$ at acute axial deviation angle $A_1$ to longitudinal axis $L_{82}$ of catheter body 82, first slit face 118 and second slit face 120 are subjected to shear forces that are resolved from longitudinal stress $\sigma_L$, when pressure differentials are created between lumen 98 and the exterior of catheter body 82, regardless of where slit valve 110 is disposed in slit orientation plane $P_1$ about longitudinal positioning point $I_1$. These shear forces that are resolved from longitudinal stress $\sigma_L$ also contribute to overcoming adhesion between molecules in material at first slit face 118 of slit valve 110 and molecules in material at slit face 120 of slit valve 110 due to intermolecular chemical bonding, intermolecular forces, and intermolecular entanglement in a similar manner as has been described previously in relation to FIGS. 13A, 13B, 14A, and 14B.

Depending on the position of slit valve 110 in slit orientation plane $P_1$ about longitudinal positioning point $I_1$, first slit face 118 and second slit face 120 can be subjected to shear forces that are resolved from radial stress $\sigma_R$ generated in outer wall 88 of catheter body 82 due to a pressure differential created between lumen 98 and the exterior of catheter body 82. The situation with regard to radial stress $\sigma_R$ will be discussed in detail subsequently in relation to FIG. 32.

Many features of catheter device 80 may be varied without departing from the teachings of the present invention. FIGS. 15-19 illustrate examples of variable aspects of the invention.

Figure 15:
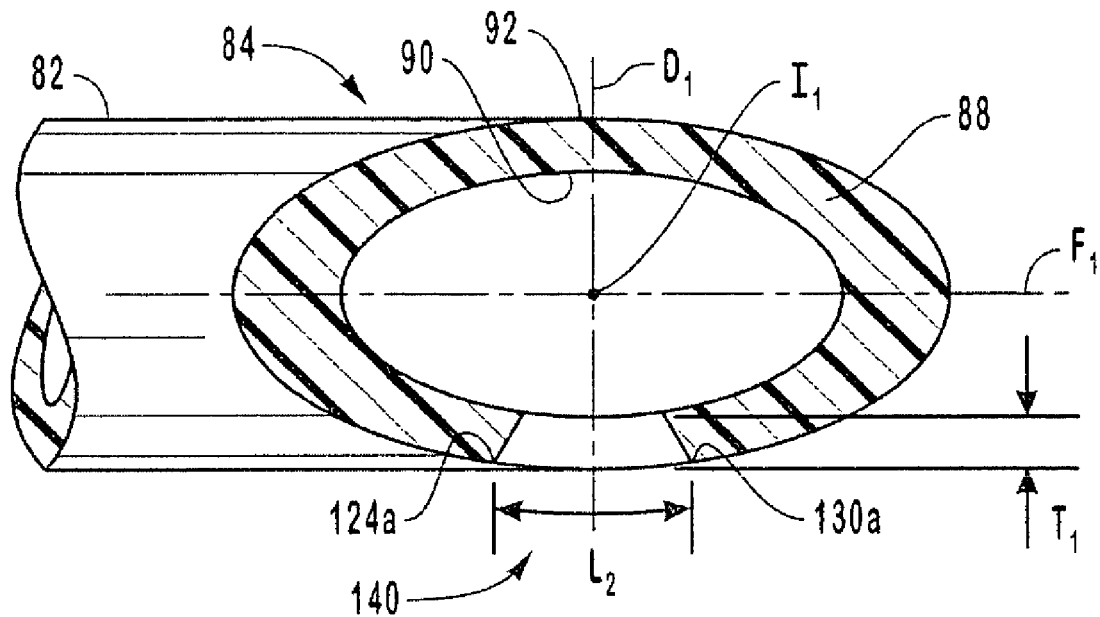
FIG. 15 is a cross-sectional view of the catheter of FIG. 10 taken along section line 11-11 shown therein illustrating a second embodiment of a slit valve incorporating teachings of the present invention.

FIG. 15 is a cross-sectional view of distal portion 84 of catheter device 80 of FIG. 10 taken along section line 11-11 shown therein illustrating a second embodiment of a slit valve 140 that incorporates teachings of the present invention. Slit valve 140 includes a planar slit having a slit length $L_2$ that is measured in the plane of slit valve 140 along outer surface 92 of catheter body 82 between outer proximal endpoint 124a and outer distal endpoint 130a, which are disposed on outer surface 92 of catheter body 82. Slit length $L_2$ is shorter than slit length $L_1$ shown in FIG. 11 and approaches the magnitude of thickness $T_1$ of outer wall 88.

Figure 16:
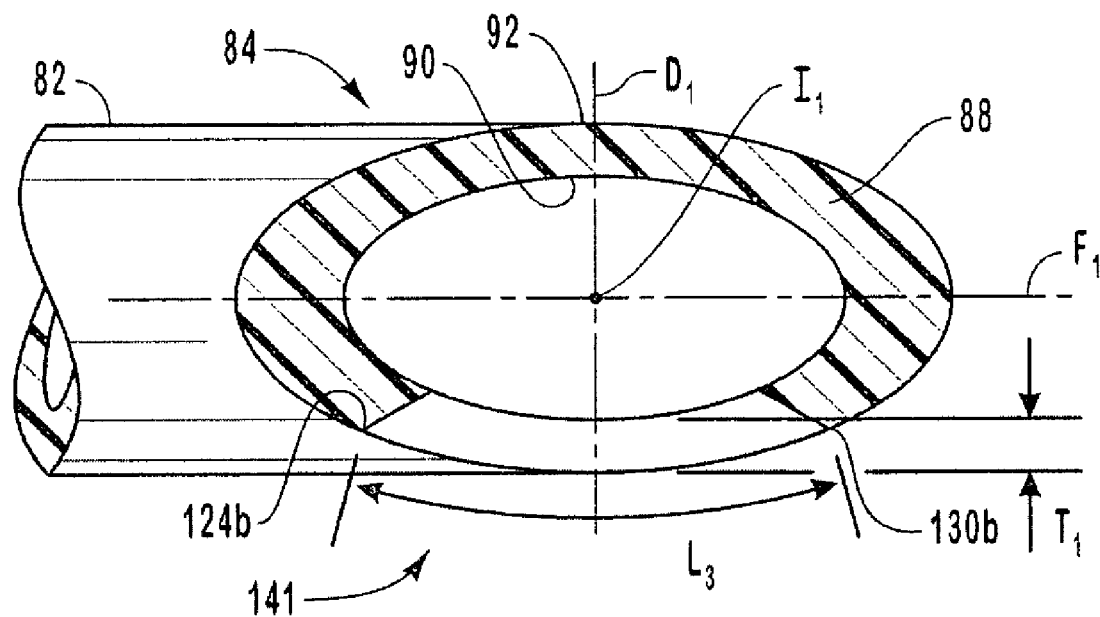
FIG. 16 is a cross-sectional view like that of FIG. 15 illustrating a third embodiment of a slit valve incorporating teachings of the present invention.

FIG. 16 is a cross-sectional view like that of FIG. 15 illustrating a third embodiment of a slit valve 141 that incorporates teachings of the present invention. Slit valve 141 includes a planar slit having a slit length $L_3$ that is measured in the plane of slit valve 141 along outer surface 92 of catheter body 82 between outer proximal endpoint 124b and outer distal endpoint 130b, which are disposed on outer surface 92 of catheter body 82. Slit length $L_3$ is approximately ten times thickness $T_1$ of outer wall 88.

Planar slit 112 of slit valve 110 shown in FIG. 12, the planar slit of slit valve 140 shown in FIG. 15, and the planar slit of slit valve 141 shown in FIG. 16 are disposed in slit orientation plane $P_1$ about longitudinal positioning point $I_1$ such that the slits are symmetric about unique diameter $D_1$. For example, the section of slit length $L_3$ shown in FIG. 16 extending between outer proximal endpoint 124b and the intersection of unique diameter $D_1$ with outer surface 92 of catheter body 82 is equal in length to the section of slit length $L_3$ extending between outer distal endpoint 130b and the intersection of unique diameter $D_1$ with outer surface 92 of catheter body 82. Nonetheless, in contrast, the position of the slit of a slit valve relative to unique diameter $D_1$ may be varied in accordance with the present invention.

Figure 17:
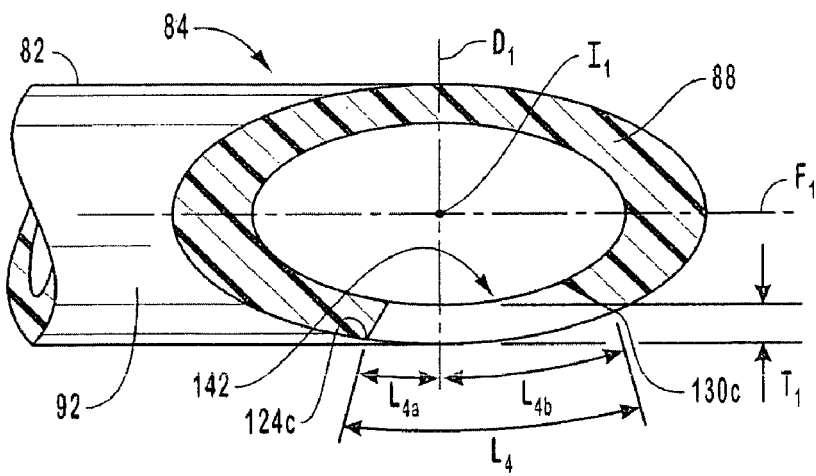
FIG. 17 is a cross-sectional view like that of FIG. 15 illustrating a fourth embodiment of a slit valve incorporating teachings of the present invention.

FIG. 17 is a cross-sectional view like that of FIG. 15 illustrating a fourth embodiment of a slit valve 142 that incorporates teachings of the present invention. Slit valve 142 is formed by a planar slit that extends through outer wall 88 of catheter body 82. Slit valve 142 has a slit length $L_4$ that is measured in the plane of slit valve 142 along outer surface 92 of catheter body 82 between outer proximal endpoint 124c and outer distal endpoint 130c, which are disposed on outer surface 92 of catheter body 82. The planar slit of slit valve 142 is disposed in slit orientation plane $P_1$ about longitudinal positioning point $I_1$ such that the slit is asymmetric about unique diameter $D_1$. In this configuration, a first slit length subsection $L_{4a}$ that extends between outer proximal endpoint 124c and the intersection of unique diameter $D_1$ with outer surface 92 of catheter body 82 is shorter than a second slit length subsection $L_{4b}$ that extends between outer distal endpoint 130c and the intersection of unique diameter $D_1$ with outer surface 92 of catheter body 82.

Figure 18:
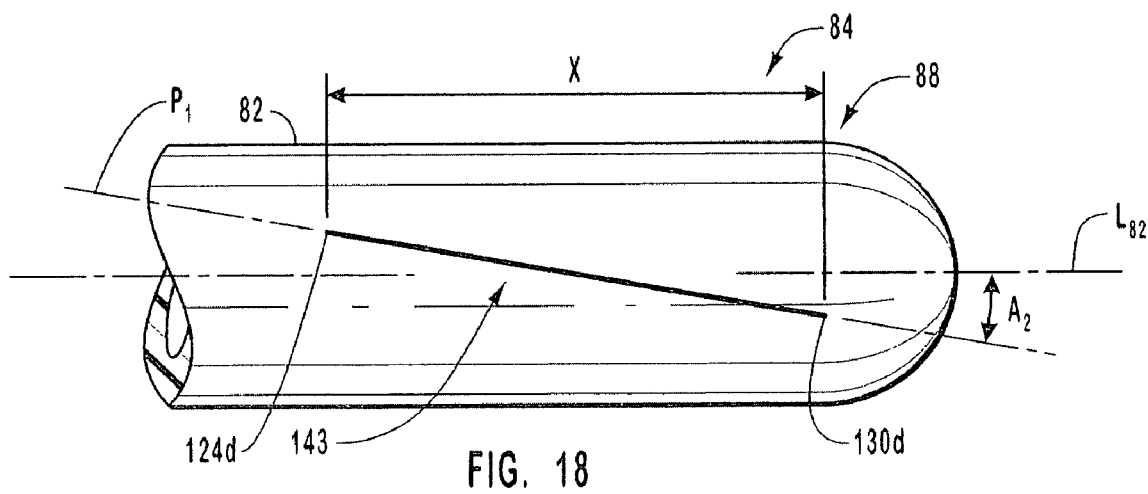
FIG. 18 is an enlarged plan view like that of FIG. 10 illustrating a fifth embodiment of a slit valve incorporating teachings of the present invention.

FIG. 18 is an enlarged plan view of distal portion 84 of catheter body 82 like that of FIG. 10 illustrating a fifth embodiment of a slit valve 143 that incorporates teachings of the present invention. Slit valve 143 is formed with a planar slit that extends through outer wall 88 of catheter body 82. The planar slit of slit valve 143 extends longitudinally along outer wall 88 of catheter body 82 between outer proximal endpoint 124d and outer distal endpoint 130d, which are disposed on outer surface 92 of catheter body 82. The planar slit of slit valve 143 is disposed in slit orientation plane $P_1$, which is oriented at an acute axial deviation angle $A_2$ of approximately 10° relative to longitudinal axis $L_{82}$ of catheter body 82. The longitudinal separation X shown in FIG. 18 between outer proximal endpoint 124d and outer distal endpoint 130d is approximately ten times thickness $T_1$ of outer wall 88 of catheter body 82 shown in FIG. 12.

Figure 19:
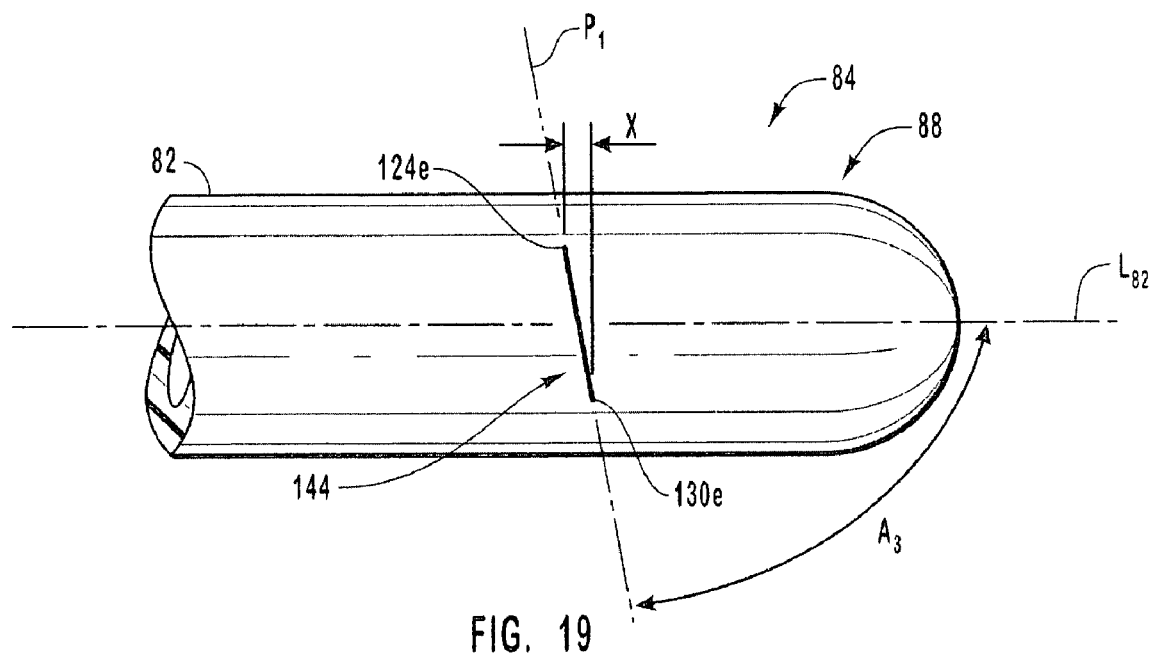
FIG. 19 is an enlarged plan view like that of FIG. 10 illustrating a sixth embodiment of a slit valve incorporating teachings of the present invention.

FIG. 19 is an enlarged plan view of distal portion 84 like that of FIG. 18 illustrating a sixth embodiment of a slit valve 144 that incorporates teachings of the present invention. Slit valve 144 is formed with a planar slit that extends through outer wall 88 of catheter body 82. The planar slit of slit valve 144 extends longitudinally along outer wall 88 of catheter body 82 between outer proximal endpoint 124e and outer distal endpoint 130e, which are disposed on outer surface 92 of catheter body 82. The planar slit of slit valve 144 is disposed in slit orientation plane $P_1$, which is oriented at an acute axial deviation angle $A_3$ of approximately 80° relative to longitudinal axis $L_{82}$ of catheter body 82. The longitudinal separation X shown in FIG. 19 between outer proximal endpoint 124e and outer distal endpoint 130e is approximately equal to thickness $T_1$ of outer wall 88 of catheter body 82 shown in FIG. 12.

Slit valve 140 of FIG. 15, slit valve 141 of FIG. 16, slit valve 142 of FIG. 17, slit valve 143 of FIG. 18, and slit valve 144 of FIG. 19 each include planar slits oriented at axial deviation angles relative to longitudinal axis $L_{82}$ of catheter body 82. As a result, shear stresses and shear forces are generated at those planar slits in outer wall 88 of catheter body 82 when pressure differentials are created between lumen 98 and the exterior of catheter body 82. These shear forces contribute to overcoming adhesion between molecules in material at one slit face of the slit valves and molecules in material at the opposing slit face of the slit valves due to intermolecular chemical bonding, intermolecular forces, and intermolecular entanglement in a similar manner as has been described previously in relation to FIGS. 13A, 13B, 14A, and 14B.

Figure 20:
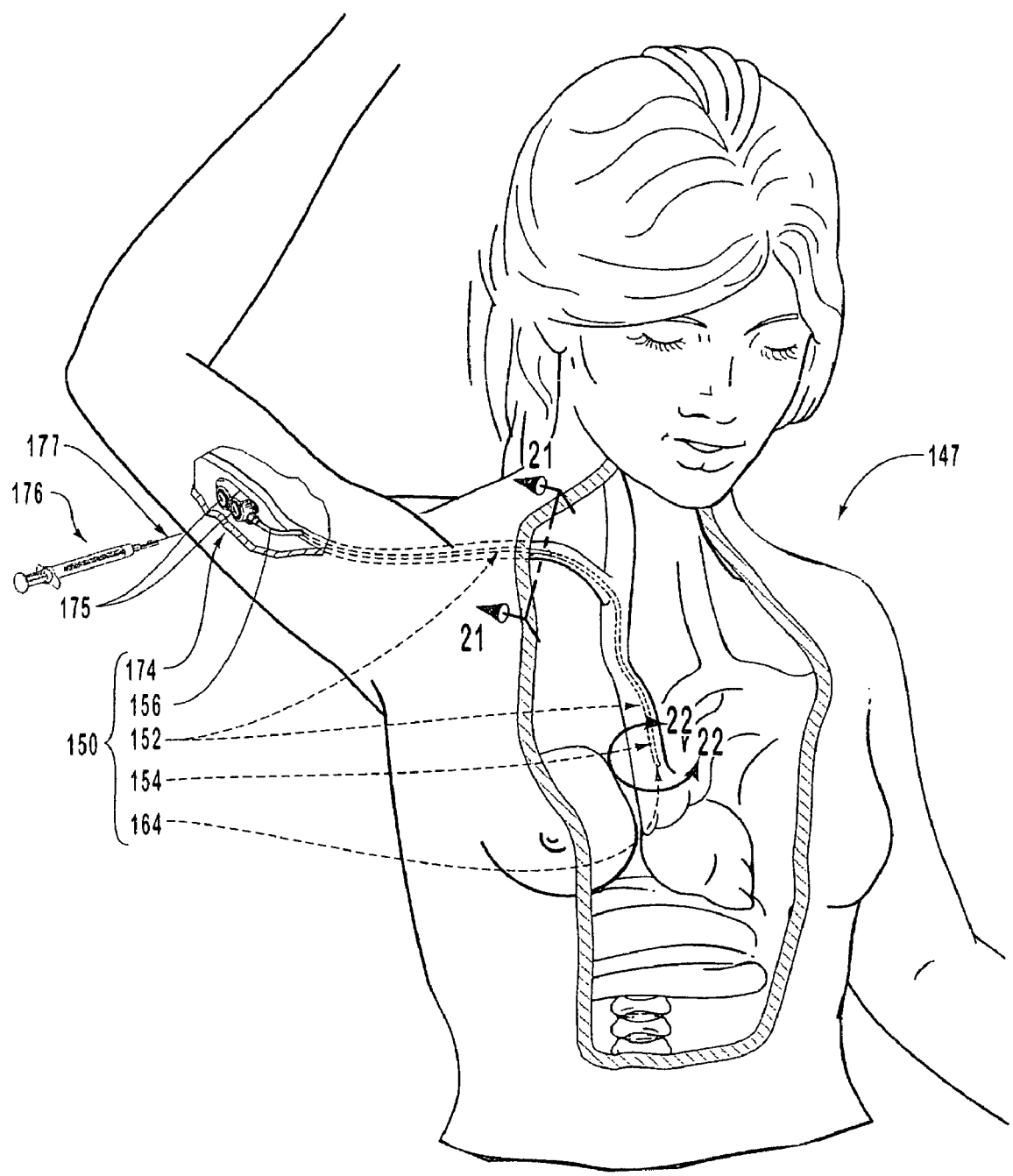
FIG. 20 is a perspective view of a third cardiovascular access system implanted in the body of a patient so as to afford transcutaneous access with a hypodermic syringe to an implanted dual reservoir access port coupled to the proximal end of a dual lumen catheter incorporating teachings of the present invention.
Figure 21:
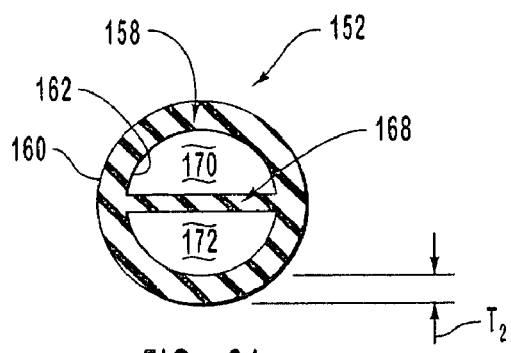
FIG. 21 is an transverse cross-sectional view of the catheter of the system of FIG. 20 taken along section line 21-21 shown therein.
Figure 22:
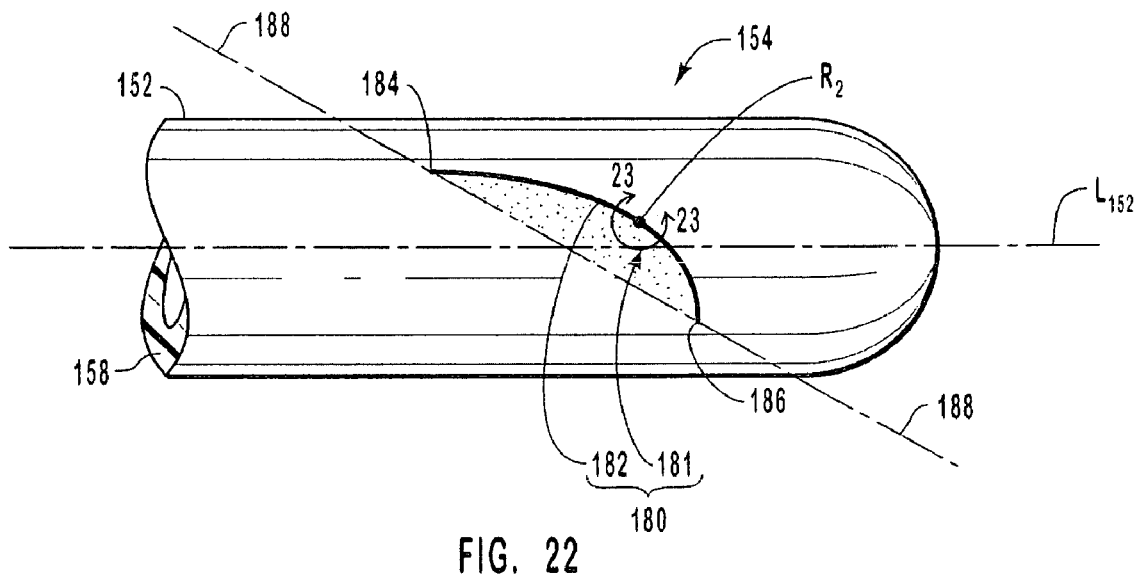
FIG. 22 is an enlarged plan view of the distal end of the catheter of FIG. 20 showing a seventh embodiment of a slit valve incorporating teachings of the present invention and being so formed as to partially circumscribe a portion of the outer wall of the illustrated catheter.

FIGS. 20-22 depict another cardiovascular access catheter device 150 that embodies teachings of the present invention.

It has been realized that the opposed slit faces of slit valves in silicone and polyurethane tubing have a tendency to adhere to each other when the opposed slit faces come into abutment with each other in the closed position of the slit valve. According to teachings of the present invention, slit valves in catheters have slit geometries so configured that when pressure differentials are applied between the interior and the exterior of a catheter the adhesion between abutting slit faces is overcome and broken in an efficient manner. In some inventive slit configurations, all or part of the slit partially circumscribes a portion of the outer wall of the catheter body adjacent to and on a first side of the slit. This reduces the restraint on the outward or inward movement of the partially circumscribed outer wall portion imposed by the portion of the outer wall on the opposite side of the slit, when pressure differentials are applied between the interior and the exterior of the body of the catheter.

FIG. 20 is a perspective view of cardiovascular access catheter device 150 implanted in the body of a patient 147 for whom a therapeutic procedure is to be undertaken on an intermittent basis, by way of example, in the superior vena cava of the venous subsystem of the cardiovascular system. Catheter device 150 includes a soft, flexible, elongated dual lumen catheter body 152 comprised of a polymeric elastomer material. For example, the polymeric elastomer material can be a polyurethane material, a silicone material, or a copolymer material.

Catheter body 152 has a distal portion 154 that is intended to reside in the superior vena cava in the body of patient 147 and a proximal end 156 that is attached to a dual-reservoir subcutaneously implantable access port 174. The entire length of catheter body 152 and access port 174 are implanted within the body of patient 147 in the same manner described previously in relation to cardiovascular access catheter device 80 of FIG. 9. A significant portion of catheter body 152 proximate distal portion 154 resides in the contiguous blood vessels extending away from the superior vena cava and into the right arm in the body of patient 147.

Dual reservoir access port 174 includes two needle-penetrable septa 175, which are comprised of a silicone material. A hypodermic syringe 176 having a needle 177 is used with catheter device 150 to infuse fluids into or aspirate fluids from the body of patient 147 in the same manner described previously in relation to syringe 104 and cardiovascular access catheter device 80 of FIG. 9.

FIG. 21 is a transverse cross-sectional view of the implanted portion of catheter body 152 of FIG. 20 taken along section line 21-21 therein. Catheter body 152 includes a cylindrical circumferential outer wall 158 and an internal septum 168 that separates a first D-shaped lumen 170 from a second D-shaped lumen 172. Outer wall 158 has an outer surface 160, an inner surface 162, and a uniform thickness $T_2$ therebetween.

FIG. 22 is an enlarged plan view of distal portion 154 of catheter body 152 of FIG. 20 that depicts a seventh embodiment of a slit valve 180 that is formed in distal portion 154 of catheter body 152 and that incorporates teachings of the present invention. Slit valve 180 includes a curved slit 182 that extends through outer wall 158 of catheter body 152 between outer surface 160 and inner surface 162 of outer wall 158 to one of first lumen 170 and second lumen 172 shown in FIG. 21. On outer surface 160 of outer wall 158 curved slit 182 extends between a proximal slit endpoint 184 and a distal slit endpoint 186. A substantial portion of curved slit 182 is disposed at an acute axial deviation angle to longitudinal axis $L_{152}$ of catheter body 152 as determined by reference to the angle between longitudinal axis $L_{152}$ and a plane tangent to each point on the substantial portion of curved slit 182.

Figure 23:
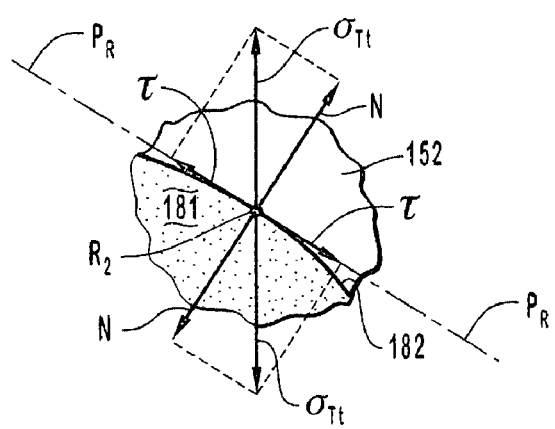
FIG. 23 is an enlarged detail view of a portion of the slit valve of FIG. 22 enhanced diagrammatically to depict components of the stresses arising at a selected point $R_2$ in the outer wall of the illustrated catheter.

FIG. 23 is an enlarged detail view of a portion of slit valve 180 illustrated in FIG. 22 at an idealized point $R_2$ of minimal extent that is traversed by curved slit 182 and that is within the substantial portion of curved slit 182 disposed at an acute axial deviation angle to longitudinal axis $L_{152}$ of catheter body 152. Plane $P_R$ is tangent to curved slit 182 at point $R_2$ and is disposed at an acute axial deviation angle to longitudinal axis $L_{152}$ of catheter body 152.

A tangential tensile stress $\sigma_{Tt}$ that is characterized by Equation No. 2 above is generated in outer wall 158 of catheter body 152 when a positive pressure differential is created between the interior and the exterior of catheter body 152. At any point in outer wall 158 of catheter body 152, tangential tensile stress $\sigma_{Tt}$ is resolvable into normal stress components and shear stress components relative to plane $P_R$. These resolved stress components are shown by way of illustration at point $R_2$ in FIG. 23. If the slit face on a first side of curved slit 182 and the slit face on the opposing side of curved slit 182 are adhered, tangential tensile stress $\sigma_{Tt}$ is resolvable at point $R_2$ into a normal stress component N that acts perpendicular to plane $P_R$, and a shear stress component T that acts parallel to plane $P_R$.

Assuming that point $R_2$ shown in FIG. 23 represents a small, finite portion of catheter body 152 traversed by curved slit 182 having known dimensions, the sum of the forces acting on point $R_2$ can be determined from the tangential tensile stress $\sigma_{Tt}$, in the manner discussed previously in relation to FIG. 13B. These forces include normal and shear forces that act on a portion of catheter body 152 on a first side of curved slit 182 that is contained by point $R_2$, and equal and opposite normal and shear forces that act on a portion of catheter body 152 on the opposite side of curved slit 182 that is contained by point $R_2$. These oppositely-directed shear forces contribute to overcoming adhesion between abutting slit faces of slit valve 180 in the same manner discussed above in relation to slit valve 110 and FIG. 13B.

Similarly, a tangential compressive stress $\sigma_{Tc}$ that is also characterized by Equation No. 2 above is generated in outer wall 158 of catheter body 152 when a negative pressure differential is created between the interior and the exterior of catheter body 152. If the slit face on a first side of curved slit 182 and the slit face on the opposing side of curved slit 182 are adhered, tangential compressive stress $\sigma_{Tc}$ is also resolvable at point $R_2$ into a normal stress component N that acts perpendicular to plane $P_R$, and a shear stress component T that acts parallel to plane $P_R$. The shear stress results from shear forces that act on a portion of catheter body 152 on a first side of curved slit 182 that is contained by point $R_2$, and equal and opposite normal and shear forces that act on a portion of catheter body 152 on the opposite side of curved slit 182 that is contained by point $R_2$. These oppositely-directed shear forces contribute to overcoming adhesion between abutting slit faces of slit valve 180 in the same manner discussed above in relation to slit valve 110 and FIG. 14B.

Shear forces contribute to overcoming adhesion between abutting slit faces of slit valve 180 by urging the slit face on a first side of curved slit 182 in a first direction parallel to plane $P_R$ and urging the slit face on the opposing side of curved slit 182 in an opposite direction to produce a shearing action between the slit faces of slit valve 180. This shearing action contributes to disrupting adhesion forces generated by intermolecular chemical bonding, intermolecular forces, and intermolecular entanglement between molecules in material at the opposing slit faces of slit valve 180. In this manner, the slit faces are urged out of sealing abutment into oppositely directed translational motion along plane $P_R$ by the shear forces. While this translational motion is so minimal as to be theoretical, it is significant on a molecular scale. The shearing process that results breaks the adhesion between the abutting slit faces and enables slit valve 180 to open outwardly in response to forces acting on outer wall 158 of catheter body 152 generated by a positive pressure differential created between the interior and the exterior of catheter body 152, and to open inwardly in response to forces acting on outer wall 158 of catheter body 152 generated by a negative pressure differential created between the interior and the exterior of catheter body 152.

As a result of the curvature of curved slit 182, slit valve 180 includes a pressure differential sensitized active valve wall member 181 that is shaded by stippling in FIG. 22. Active valve wall member 181 is integrally formed with catheter body 152 and partially circumscribed by curved slit 182. As shown in FIG. 22, active valve wall member 181 projects laterally beyond a support line 188 shown in phantom that is defined by proximal slit endpoint 184 and distal slit endpoint 186. Active valve wall member 181 thus forms a cantilevered portion of catheter body 152 that is supported along support line 188 and unsupported along curved slit 182, once adhesion between the slit face on a first side of curved slit 182 and the slit face on the opposing side of curved slit 182 is overcome. The curved shape of curved slit 182 reduces the restraint to outward and inward movement imposed on active valve wall member 181 by the portion of outer wall 158 of catheter body 152 on the side of curved slit 182 opposite from active valve wall member 181. Thus, by partially circumscribing active valve wall member 181, restraint to outward and inward movement of active valve wall member 181 imposed by adjacent portions of catheter body 152 is reduced.

Active valve wall member 181 arches outwardly or inwardly from support line 188 in a manner similar to the movement of a hinge when slit valve 180 is moved from the closed position to an open position thereof. A positive pressure differential created between the interior and the exterior of catheter body 152 will generate outwardly-directed forces that act on outer wall 158 of catheter body 152. These outwardly-directed forces urge active valve wall member 181 in a radially outward direction, thereby causing slit valve 180 to assume an outwardly open configuration. A negative pressure differential created between the interior and the exterior of catheter body 152 will generate inwardly-directed forces that act on outer wall 158 of catheter body 152. These inwardly-directed forces urge active valve wall member 181 in a radially inward direction, thereby causing slit valve 180 to assume an inwardly open configuration.

Many features of catheter device 150 may be varied without departing from the scope of the present invention. FIGS. 24-27 illustrate examples of variable aspects of the invention.

Figure 24:
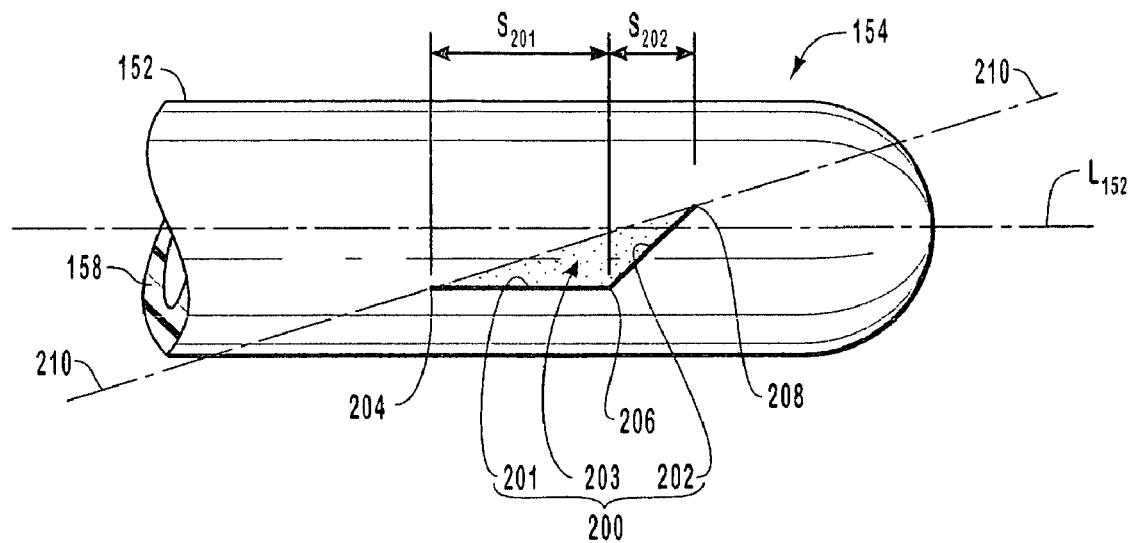
FIG. 24 is an enlarged plan view like that of FIG. 22 showing an eighth embodiment of a slit valve incorporating teachings of the present invention and assuming the form of a compound slit valve that partially circumscribes a portion of the outer wall of the illustrated catheter.

FIG. 24 is an enlarged plan view like that of FIG. 22 showing an eighth embodiment of a slit valve 200 that incorporates teachings of the present invention. Compound slit valve 200 is formed in distal portion 154 of catheter body 152 and includes a first slit section $S_{201}$ and a second slit section $S_{202}$. First slit section $S_{201}$ includes a planar slit 201 that is disposed in a plane containing longitudinal axis $L_{152}$ of catheter body 152. Planar slit 201 extends along outer surface 160 between a proximal slit endpoint 204 and a slit midpoint 206. Second slit section $S_{202}$ includes a planar slit 202 that is disposed in a plane oriented at an acute axial deviation angle relative to longitudinal axis $L_{152}$ of catheter body 152 in the same manner discussed above in relation to slit valve 110 of FIG. 10. Planar slit 202 adjoins to and is continuous with the distal end of planar slit 201 and extends along outer surface 160 between slit midpoint 206 and a distal slit endpoint 208. Slit midpoint 206 is a distal endpoint for first slit section $S_{201}$ and a proximal endpoint for second slit section $S_{202}$.

By orienting planar slit 202 at an acute axial deviation angle relative to longitudinal axis $L_{152}$ of catheter body 152, planar slit 202 contributes to overcoming adhesion between abutting slit faces of slit valve 200 in the same manner discussed above in relation to slit valve 110 and FIGS. 13A, 13B, 14A, and 14B.

First slit section $S_{201}$ and second slit section $S_{202}$ partially circumscribe a pressure differential sensitized active valve wall member 203 that is otherwise integrally formed with catheter body 152. As shown in FIG. 24, active valve wall member 203 projects laterally beyond a support line 210 shown in phantom that is defined by proximal slit endpoint 204 and distal slit endpoint 208. Active valve wall member 203 thus forms a cantilevered portion of the catheter body 152 that is supported along support line 210 and unsupported along first slit section $S_{201}$ and second slit section $S_{202}$ once adhesion between the slit faces of compound slit valve 200 is overcome.

The overall curved slit path formed by planar slit 201 and planar slit 202 together between proximal slit endpoint 204 and distal slit endpoint 208 reduces the restraint to outward and inward movement imposed on active valve wall member 203 by the portion of outer wall 158 of catheter body 152 on the sides of planar slit 201 and planar slit 202 opposite from active valve wall member 203. Thus, by partially circumscribing active valve wall member 203, restraint to outward and inward movement of active valve wall member 203 imposed by adjacent portions of catheter body 152 is reduced.

Figure 25:
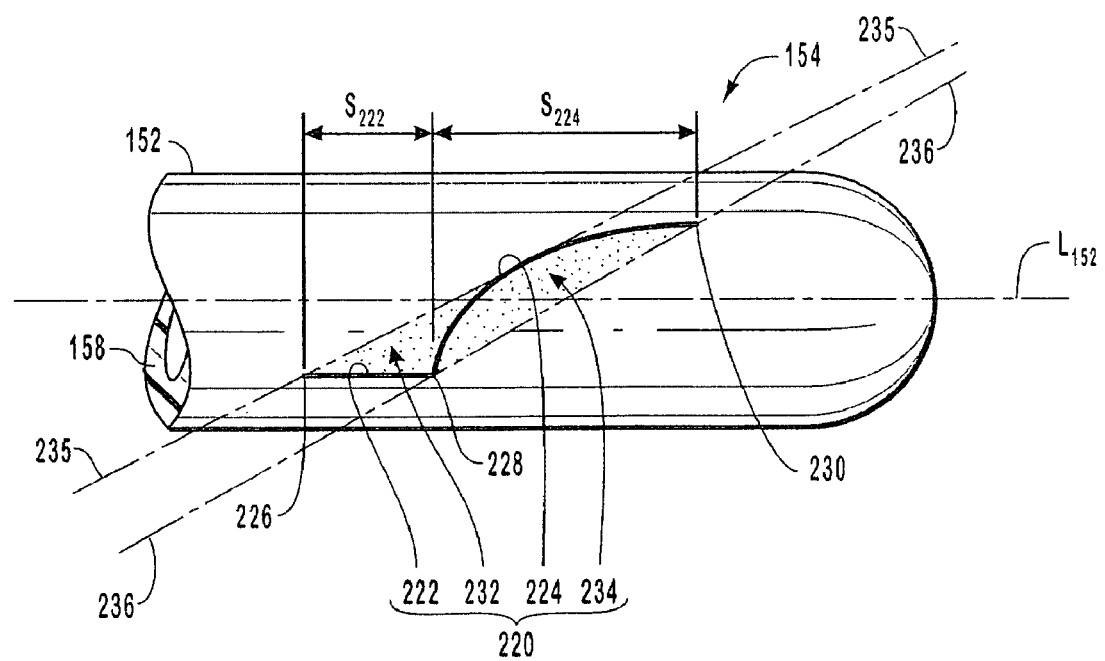
FIG. 25 is an enlarged plan view like that of FIG. 22 showing a ninth embodiment of a slit valve incorporating teachings of the present invention and assuming the form of a compound slit valve that partially circumscribes a plurality of portions of the outer wall of the illustrated catheter.

FIG. 25 is an enlarged plan view like that of FIG. 22 showing a ninth embodiment of a slit valve 220 that incorporates teachings of the present invention. Compound slit valve 220 is formed in distal portion 154 of catheter body 152 and includes a first slit section $S_{222}$ and a second slit section $S_{224}$. First slit section $S_{222}$ includes a planar slit 222 that is disposed in a plane containing longitudinal axis $L_{152}$ of catheter body 152. Slit 222 extends along outer surface 160 between a proximal slit endpoint 226 and a slit midpoint 228. Second slit section $S_{224}$ includes a curved slit 224, a substantial portion of which is disposed at an acute axial deviation angle to longitudinal axis $L_{152}$ of catheter body 152, as determined by reference to the angle between longitudinal axis $L_{152}$ and a plane tangent to each point along curved slit 224. Curved slit 224 adjoins to and is continuous with the distal end of planar slit 222, extending along outer surface 160 between slit midpoint 228 and a distal slit endpoint 230. Slit midpoint 228 and distal slit endpoint 230 are so located on outer surface 160 of catheter body 152 as to avoid defining therebetween on outer surface 160 a line parallel to longitudinal axis $L_{152}$ of catheter body 152. Slit midpoint 228 is a distal endpoint for first slit section $S_{222}$ and a proximal endpoint for second slit section $S_{224}$.

Alternatively, curved slit 224 could be configured such that second slit section $S_{224}$ would appear as a fraction of a circumference of a circle on outer surface 160 of catheter body 152. Planar slit 222 could be disposed in a plane that is oriented at an acute axial deviation angle to longitudinal axis $L_{152}$ of catheter body 152.

Because a substantial portion of curved slit 224 is disposed at an acute axial deviation angle to longitudinal axis $L_{152}$ of catheter body 152, curved slit 224 contributes to overcoming adhesion between abutting slit faces of slit valve 220 in the same manner discussed above in relation to slit valve 180 of FIG. 22.

First slit section $S_{222}$ and a proximal portion of second slit section $S_{224}$ partially circumscribe a first pressure differential sensitized active valve wall member 232 that is otherwise integrally formed with catheter body 152. As shown in FIG. 25, first active valve wall member 232 projects laterally beyond a first support line 235 shown in phantom that is tangent to curved second slit section $S_{224}$ and passes through proximal slit endpoint 226. First active valve wall member 232 thus forms a cantilevered portion of catheter body 152 that is supported along first support line 235 and unsupported along first slit section $S_{222}$ and a proximal portion of second slit section $S_{224}$ once adhesion between the slit faces of compound slit valve 220 is overcome.

The overall curved path formed by planar slit 222 and a proximal portion of curved slit 224 between proximal slit endpoint 226 and the point at which first support line 235 is tangent to curved slit 224 reduces the restraint to outward and inward movement imposed on active valve wall member 232 by the portion of outer wall 158 of catheter body 152 on the sides of planar slit 222 and curved slit 224 opposite from active valve wall member 232. Thus, by partially circumscribing active valve wall member 232, restraint to outward and inward movement of active valve wall member 232 imposed by adjacent portions of catheter body 152 is reduced.

Second slit section $S_{224}$ partially circumscribes a second pressure differential sensitized active valve wall member 234 that is otherwise integrally formed with catheter body 152. As shown in FIG. 25, second active valve wall member 234 projects laterally beyond a second support line 236 that is defined by slit midpoint 228 and distal slit endpoint 230. Second active valve wall member 234 thus forms a cantilevered portion of catheter body 152 that is supported along second support line 236 and unsupported along curved second slit section $S_{224}$ once adhesion between the slit faces of compound slit valve 220 is overcome.

The curved shape of curved slit 224 reduces the restraint to outward and inward movement imposed on active valve wall member 234 by the portion of outer wall 158 of catheter body 152 on the side of curved slit 224 opposite from active valve wall member 234. Thus, by partially circumscribing active valve wall member 234, restraint to outward and inward movement of active valve wall member 234 imposed by adjacent portions of catheter body 152 is reduced.

Alternatively, second slit section $S_{224}$ could include a plurality of planar slit subsections or a plurality of curved slit subsections. These slit subsections would be arranged in an end-to-end relationship to form a generally curved overall configuration. In another configuration, second slit section $S_{224}$ can include a planar portion connected to a curved portion that together form a generally curved overall slit section.

Figure 26:
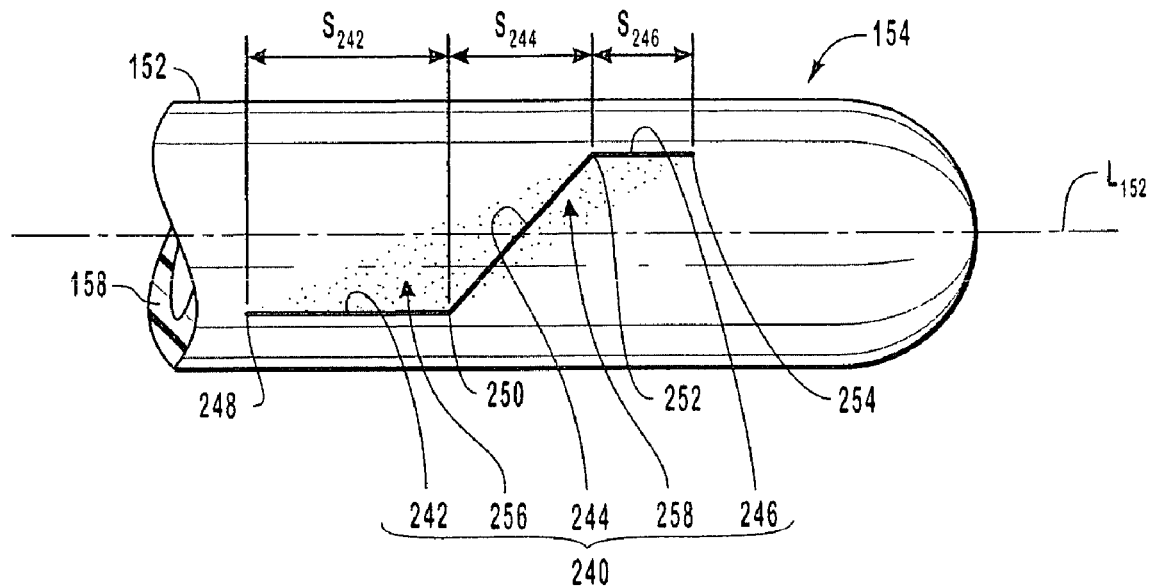
FIG. 26 is an enlarged plan view like that of FIG. 22 showing a tenth embodiment of a slit valve incorporating teachings of the present invention and assuming the form of a compound slit valve that partially circumscribes a plurality of portions of the outer wall of the illustrated catheter.

FIG. 26 is an enlarged plan view like that of FIG. 22 showing a tenth embodiment of a slit valve 240 that incorporates teachings of the present invention. Compound slit valve 240 is formed in distal portion 154 of catheter body 152 and includes a first slit section $S_{242}$, a second slit section $S_{244}$, and a third slit section $S_{246}$. First slit section $S_{242}$ includes a planar slit 242 that is disposed in a plane containing longitudinal axis $L_{152}$ of catheter body 152. Planar slit 242 extends along outer surface 160 between a proximal slit endpoint 248 and a proximal slit midpoint 250. Second slit section $S_{244}$ includes a planar slit 244 that is disposed in a plane oriented at an acute axial deviation angle relative to longitudinal axis $L_{152}$ of catheter body 152. Planar slit 244 adjoins to and is continuous with the distal end of slit 242, extending along outer surface 160 between proximal slit midpoint 250 and a distal slit midpoint 252. Third slit section $S_{246}$ includes a planar slit 246 that is disposed in a plane containing longitudinal axis $L_{152}$ of catheter body 152. Planar slit 246 adjoins to and is continuous with the distal end of planar slit 244, extending along outer surface 160 between distal slit midpoint 252 and a distal slit endpoint 254.

Proximal slit midpoint 250 is a distal endpoint for first slit section $S_{242}$ and a proximal endpoint for second slit section $S_{244}$. Distal slit midpoint 252 is a distal endpoint for second slit section $S_{244}$ and a proximal endpoint for third slit section $S_{246}$.

By orienting planar slit 244 at an acute axial deviation angle relative to longitudinal axis $L_{152}$ of catheter body 152, planar slit 244 contributes to overcoming adhesion between abutting slit faces of slit valve 240 in the same manner discussed above in relation to slit valve 110 and FIGS. 13A, 13B, 14A, and 14B.

First slit section $S_{242}$ and second slit section $S_{244}$ partially circumscribe a first pressure differential sensitized active valve wall member 256 that is otherwise integrally formed with catheter body 152. Second slit section $S_{244}$ and third slit section $S_{246}$ partially circumscribe a second pressure differential sensitized active valve wall member 258 that is otherwise integrally formed with catheter body 152.

The overall curved path formed by planar slit 242 and planar slit 244 between proximal slit endpoint 248 and distal slit midpoint 252 reduces the restraint to outward and inward movement imposed on active valve wall member 256 by the portion of outer wall 158 of catheter body 152 on the sides of planar slit 242 and planar slit 244 opposite from active valve wall member 256 in the same manner discussed above in relation to slit valve 200 of FIG. 24. The overall curved path formed by planar slit 244 and planar slit 246 between proximal slit midpoint 250 and distal slit endpoint 254 reduces the restraint to outward and inward movement imposed on active valve wall member 258 by the portion of outer wall 158 of catheter body 152 on the sides of planar slit 244 and planar slit 246 opposite from active valve wall member 258 in the same manner discussed above in relation to slit valve 200 of FIG. 24.

Figure 27:
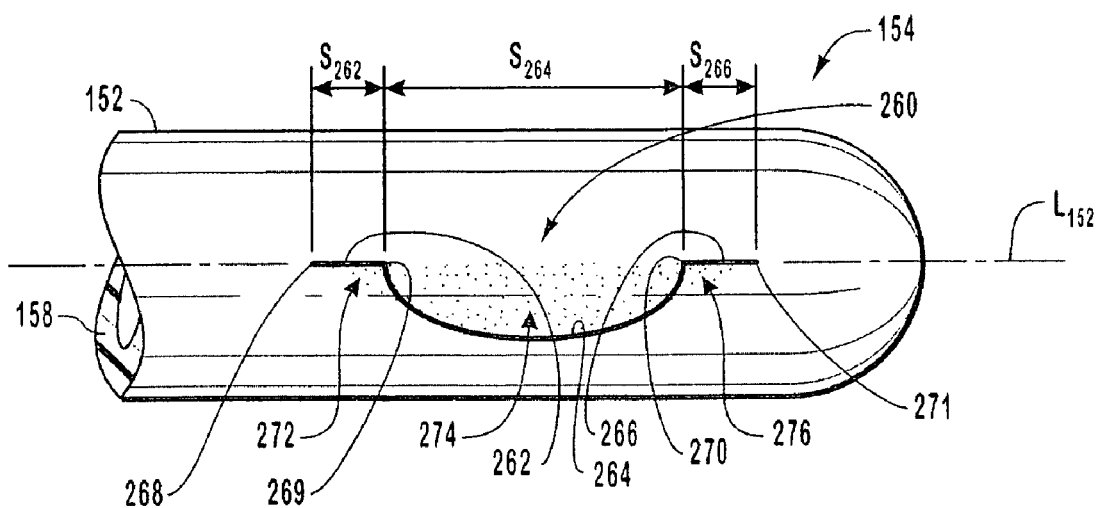
FIG. 27 is an enlarged plan view like that of FIG. 22 showing an eleventh embodiment of a slit valve incorporating teachings of the present invention and assuming the form of a compound slit valve that partially circumscribes a plurality of portions of the outer wall of the illustrated catheter.

FIG. 27 is an enlarged plan view like that of FIG. 22 showing an eleventh embodiment of a slit valve incorporating teachings of the present invention. A compound slit valve 260 is formed in distal portion 154 of catheter body 152 and includes a first slit section $S_{262}$, a second slit section $S_{264}$, and a third slit section $S_{266}$.

First slit section $S_{262}$ includes a planar slit 262 that is disposed in a plane containing longitudinal axis $L_{152}$ of catheter body 152. Planar slit 262 extends along outer surface 160 between a proximal slit endpoint 268 and a proximal slit midpoint 269. Second slit section $S_{264}$ includes a curved slit 264, a substantial portion of which is disposed at an acute axial deviation angle to longitudinal axis $L_{152}$, as determined by reference to the angle between longitudinal axis $L_{152}$ and a plane tangent to each point along curved slit 264. Curved slit 264 adjoins to and is continuous with the distal end of planar slit 262, extending along outer surface 160 between proximal slit midpoint 269 and a distal slit midpoint 270. Proximal slit midpoint 269 and distal slit midpoint 270 are so located on outer surface 160 of catheter body 152 as to define therebetween on outer surface 160 a line parallel to longitudinal axis $L_{152}$ of catheter body 152. Third slit section $S_{266}$ includes a planar slit 266 that is disposed in the plane containing planar slit 262 and longitudinal axis $L_{152}$. Planar slit 266 adjoins to and is continuous with the distal end of curved slit 264, extending along outer surface 160 between distal slit midpoint 270 and a distal slit endpoint 271.

Proximal slit midpoint 269 is a distal endpoint for first slit section $S_{262}$ and a proximal endpoint for second slit section $S_{264}$. Distal slit midpoint 270 is a distal endpoint for second slit section $S_{264}$ and a proximal endpoint for third slit section $S_{266}$.

Alternatively, third slit section $S_{266}$ could include a planar slit 266 that is disposed in an additional plane containing longitudinal axis $L_{152}$ and intersecting the plane containing planar slit 262 along the longitudinal axis $L_{152}$ of catheter body 152. Second slit section $S_{264}$ could include a plurality of planar sub-sections a plurality of curved sub-sections. The slit sub-sections could be arranged end-to-end to form a generally curved configuration. In another configuration, second slit section $S_{264}$ could include a planar portion and a curved portion that together form a generally curved slit section.

Because a substantial portion of curved slit 264 is disposed at an acute axial deviation angle to longitudinal axis $L_{152}$ of catheter body 152, curved slit 264 contributes to overcoming adhesion between abutting slit faces of slit valve 260 in the same manner discussed above in relation to slit valve 180 of FIG. 22.

First slit section $S_{262}$ and a proximal portion of curved second slit section $S_{264}$ partially circumscribe a first pressure differential sensitized active valve wall member 272 that is otherwise integrally formed with catheter body 152. Curved second slit section S264 partially circumscribes a second pressure differential sensitized active valve wall member 274 that is otherwise integrally formed with catheter body 152. Third slit section $S_{266}$ and a distal portion of curved second slit section $S_{264}$ partially circumscribe a third pressure differential sensitized active valve wall member 276 that is otherwise integrally formed with catheter body 152. The restraint to outward and inward movement imposed on first active valve wall member 272, second active valve wall member 274, and third active valve wall member 276 by adjacent portions of outer wall 158 of catheter body 152 is reduced in the same manner discussed above in relation to slit valve 180 of FIG. 22, slit valve 200 of FIG. 24, slit valve 220 of FIG. 25, and slit valve 240 of FIG. 26.

Slit valve 180 of FIG. 22, compound slit valve 200 of FIG. 24, compound slit valve 220 of FIG. 25, compound slit valve 240 of FIG. 26, and compound slit valve 260 of FIG. 27 each include a slit having a substantial portion thereof oriented at an acute axial deviation angle relative to longitudinal axis $L_{152}$ of catheter body 152. These embodiments of slit valves overcome adhesion due to intermolecular chemical bonding, intermolecular forces, and intermolecular entanglement between molecules in material at the opposing slit faces of the slit valves in a similar manner as that discussed previously in relation to slit valve 110 of FIG. 10. Because a substantial portion of each slit is oriented at an acute axial deviation angle relative to the longitudinal axis of the catheter body, shear forces parallel to the slit faces are generated in response to positive and negative pressure differentials created between the interior and the exterior of catheter body 152. The slit valves also each include pressure differential sensitized active valve wall members that are partially circumscribed by the slit or slits of each slit valve to reduce the restraint to outward and inward movement imposed on each active valve wall member by portions of outer wall 158 of catheter body 152 on the opposite side of each slit from each active valve wall member.

Each of the embodiments of the present invention disclosed previously includes a two-way, three-position slit valve formed in the body of a catheter. Nonetheless, one-way, two-position slit valves formed in the body of a catheter can also embody teachings of the present invention.

For example, FIGS. 28-36 depict a cardiovascular access catheter device that includes an elongated catheter body 282 with a distal portion 284 having a closed distal tip 286. Elongated catheter body 282 is formed from a polymeric elastomer material. For example, the polymeric elastomer material can be a polyurethane material, a silicone material, or a copolymer material. Formed in the outer wall 287 of distal portion 284 are two complementary, operationally oppositely biased one-way, two-position slit valves that each includes a pair of slits. Each of the slit valves incorporates teachings of the present invention. To permit the infusion of fluid into the body of a patient, a first one-way, two-position valve is configured to open exclusively outwardly, typically in response to a positive pressure differential created between a lumen in the catheter body and the exterior thereof. In complement thereto, a second one-way, two-position valve is configured to open exclusively inwardly, typically in response to a negative pressure differential created between that same lumen of the catheter body and the exterior thereof to permit the aspiration of fluid from the body of a patient.

Figure 28:
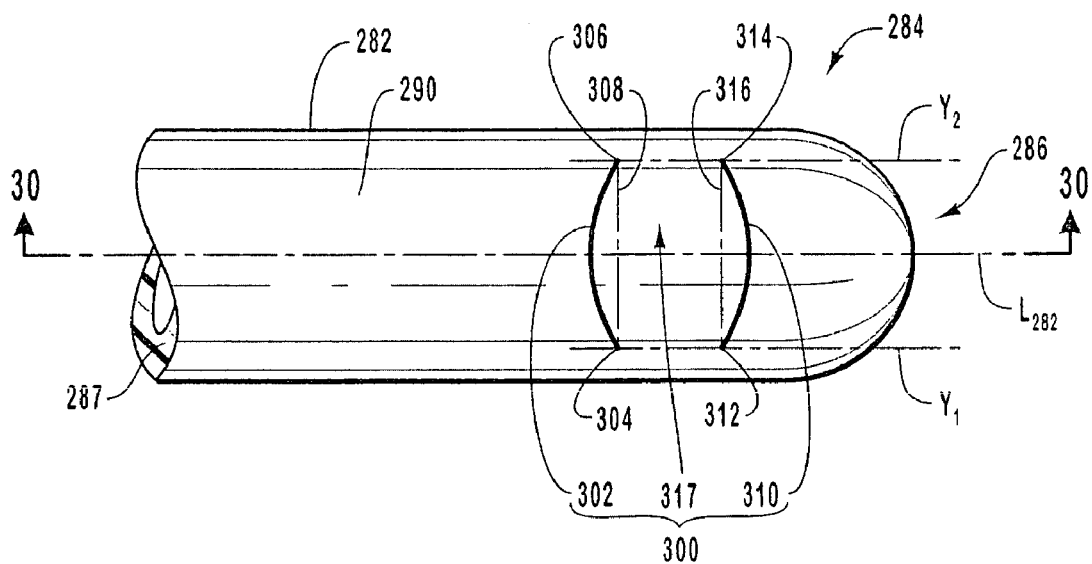
FIG. 28 is an enlarged plan view of the distal portion of a single lumen catheter showing an infusion valve formed in the outer wall thereof that incorporates teachings of the present invention.

FIG. 28 is an enlarged plan view of distal portion 284 illustrating a twelfth embodiment of a slit valve that incorporates teachings of the present invention and that assumes the form of a one-way, two-position infusion valve 300 formed through the outer wall 287 of catheter body 282. Infusion valve 300 includes a planar proximal infusion slit 302 that extends on the outer surface 290 of catheter body 282 between a first proximal infusion endpoint 304 and a second proximal infusion endpoint 306. First proximal infusion endpoint 304 and second proximal infusion endpoint 306 define the endpoints of a circumferential proximal infusion arc 308 on outer surface 290. Circumferential proximal infusion arc 308 is disposed in a plane that contains first proximal infusion endpoint 304 and second proximal infusion endpoint 306 and that is perpendicular to longitudinal axis $L_{282}$ of catheter body 282. Infusion valve 300 also includes a planar distal infusion slit 310 that extends on outer surface 290 between a first distal infusion endpoint 312 and a second distal infusion endpoint 314. First distal infusion endpoint 312 and second distal infusion endpoint 314 define the endpoints of a circumferential distal infusion arc 316 on outer surface 290. Circumferential distal infusion arc 316 is disposed in a plane that contains first distal infusion endpoint 312 and second distal infusion endpoint 314 and that is perpendicular to longitudinal axis $L_{282}$ of catheter body 282.

Figure 30:
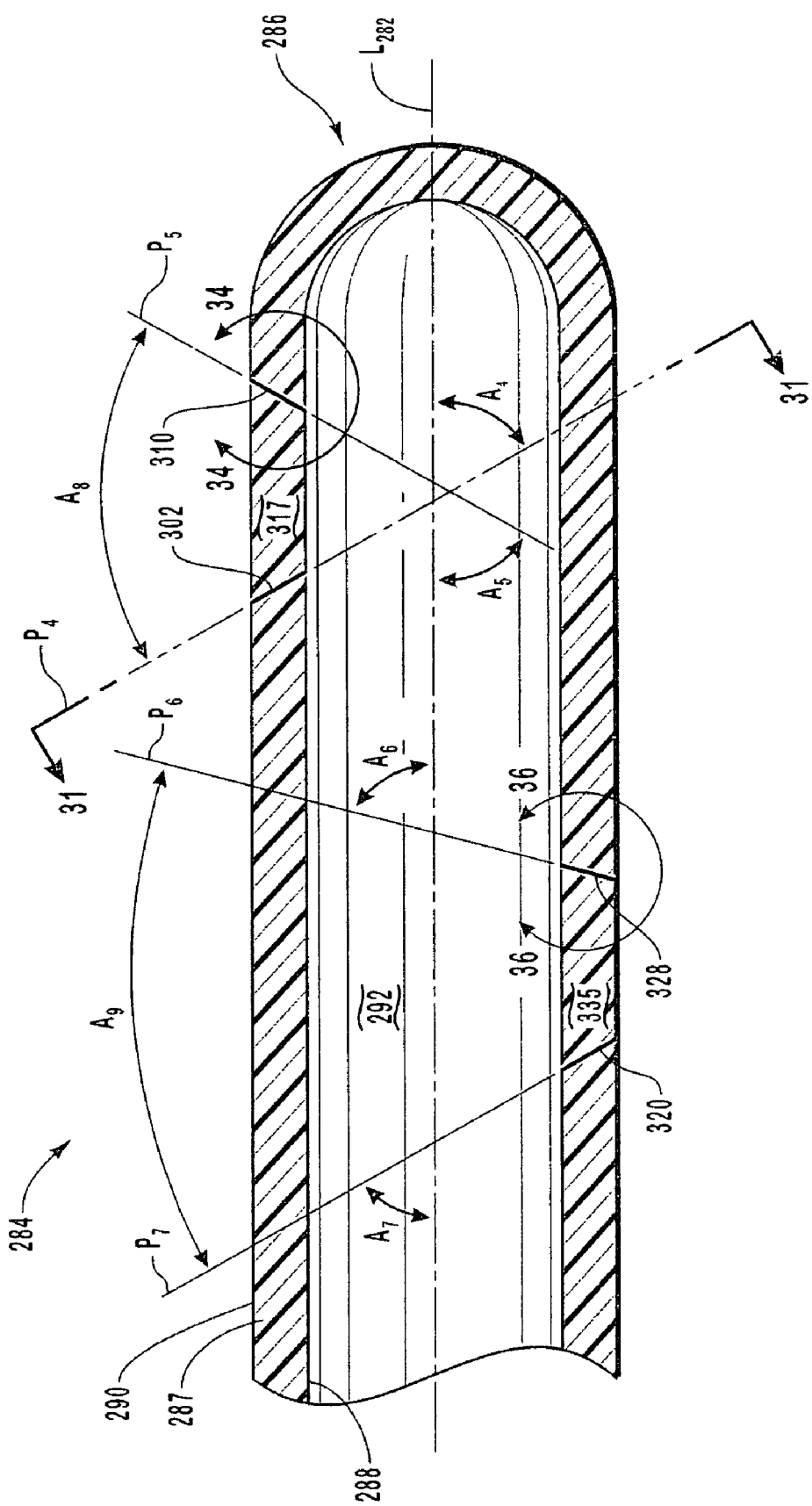
FIG. 30 is a longitudinal cross-sectional view of the catheter of FIGS. 28-29 taken along section line 30-30 shown in FIG. 28.

First proximal infusion endpoint 304 and first distal infusion endpoint 312 are so located on outer surface 290 of catheter body 282 as to define therebetween on outer surface 290 a first line $Y_1$ that is parallel to longitudinal axis $L_{282}$ of catheter body 282. Second proximal infusion endpoint 306 and second distal infusion endpoint 314 are so located on outer surface 290 of catheter body 282 as to define therebetween on outer surface 290 a second line $Y_2$ that is parallel to longitudinal axis $L_{282}$ of catheter body 282. In FIG. 30, proximal infusion slit 302 and distal infusion slit 310 appear as curves that each extend in laterally symmetric fashion between first line $Y_1$ and second line $Y_2$ about longitudinal axis $L_{282}$ on outer surface 290 of catheter body 282.

Between proximal infusion slit 302 and distal infusion slit 310, a pressure differential sensitized active valve wall member 317 results that is integrally formed with catheter body 282 but that is partially circumscribed at the opposed proximal and distal ends thereof, respectively, by proximal infusion slit 302 and distal infusion slit 310. The portion of active valve wall member 317 that is disposed between proximal infusion slit 302 and circumferential proximal infusion arc 308 is partially circumscribed by proximal infusion slit 302 and operates as a smaller active valve wall member on its own. The portion of active valve wall member 317 that is disposed between distal infusion slit 310 and circumferential distal infusion arc 316 is partially circumscribed by distal infusion slit 310 and also operates as a smaller active valve wall member on its own. By partially circumscribing active valve wall member 317, proximal infusion slit 302 and distal infusion slit 310 reduce the restraint to outward movement of active valve wall member 317 imposed by portions of catheter body 282 that are adjacent to active valve wall member 317.

Figure 29:
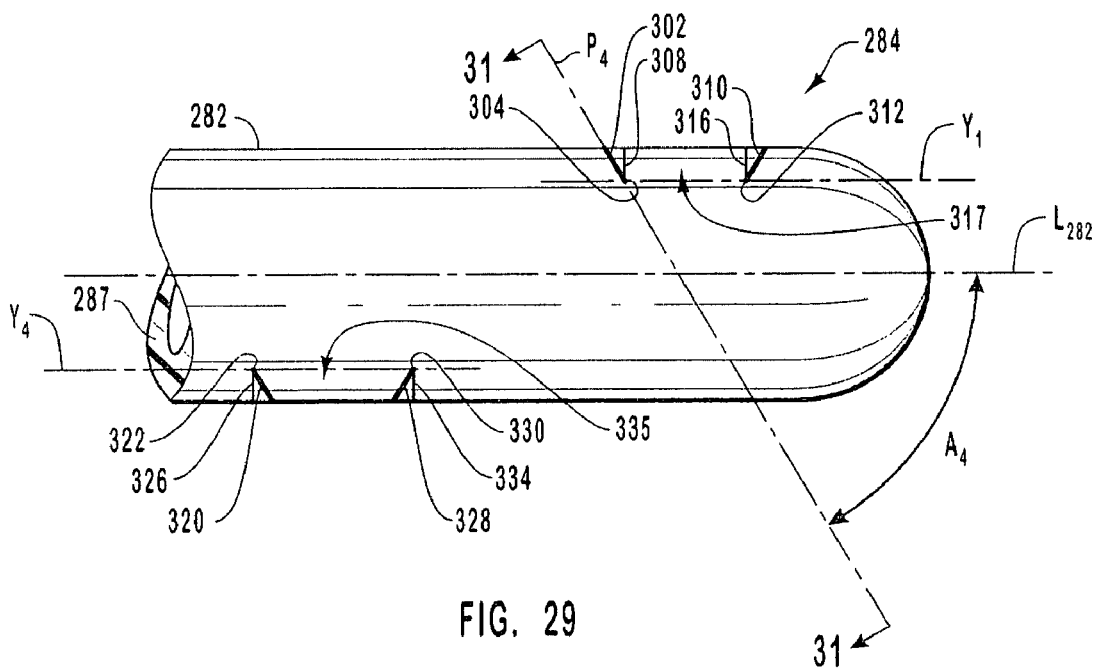
FIG. 29 is an elevation view of the distal portion of the catheter illustrated in FIG. 28.

FIG. 29 is an elevation view of distal portion 284 of catheter body 282 of FIG. 28. As seen in FIG. 29, a one-way, two-position aspiration valve 318 is formed on the side of catheter body 282 opposite infusion valve 300. One-way, two-position aspiration valve 318 will be discussed subsequently in further detail after completion of a discussion of one-way, two-position infusion valve 300.

FIG. 30 is a longitudinal cross-sectional view of distal portion 284 of catheter body 282 of FIGS. 28-29 taken along section line 30-30 shown in FIG. 28. As seen in FIG. 30, catheter body 282 includes outer surface 290, an inner surface 288, and encloses a longitudinally extending fluid flow lumen 292 that is closed at the distal end thereof. Planar proximal infusion slit 302 is contained in a proximal infusion slit orientation plane $P_4$ that is oriented at an acute axial deviation angle $A_4$ to longitudinal axis $L_{282}$ of catheter body 282, while planar distal infusion slit 310 is contained in a distal infusion slit orientation plane $P_5$ that is oriented at an acute axial deviation angle $A_5$ to longitudinal axis $L_{282}$ of catheter body 282. As distal infusion slit orientation plane $P_5$ is not parallel to proximal infusion slit orientation plane $P_4$, proximal infusion slit orientation plane $P_4$ is oriented at a divergence angle $A_8$ relative to distal aspiration slit orientation plane $P_5$. Broadly, acute axial deviation angle $A_4$ and acute axial deviation angle $A_5$ may be in a range from about 10° to about 80°. More narrowly, acute axial deviation angle $A_4$ and acute axial deviation angle $A_5$ may be in a range from about 20° to about 70°. Most narrowly, acute axial deviation angle $A_4$ and acute axial deviation angle $A_5$ may be in a range from about 30° to about 60°. Acute axial deviation angle $A_5$ may be equal to or differ from acute axial deviation angle $A_4$.

As shown in FIG. 30, the longitudinal cross section of active valve wall member 317 assumes a trapezoidal configuration having the longer of the parallel sides thereof on outer surface 290 of outer wall 287 of catheter body 282 and the shorter of the parallel sides on the inner surface 288 of outer wall 287 of catheter body 282, adjacent to lumen 292. This produces in the longitudinal cross section of active valve wall member 317 a wedge shape that facilitates the outward movement of active valve wall member 317 in response to a positive pressure differential, while precluding inward movement of active valve wall member 317 in response to a negative pressure differential. In this manner, infusion valve 300 operates as an outwardly-opening one-way, two-position valve.

Figure 31:
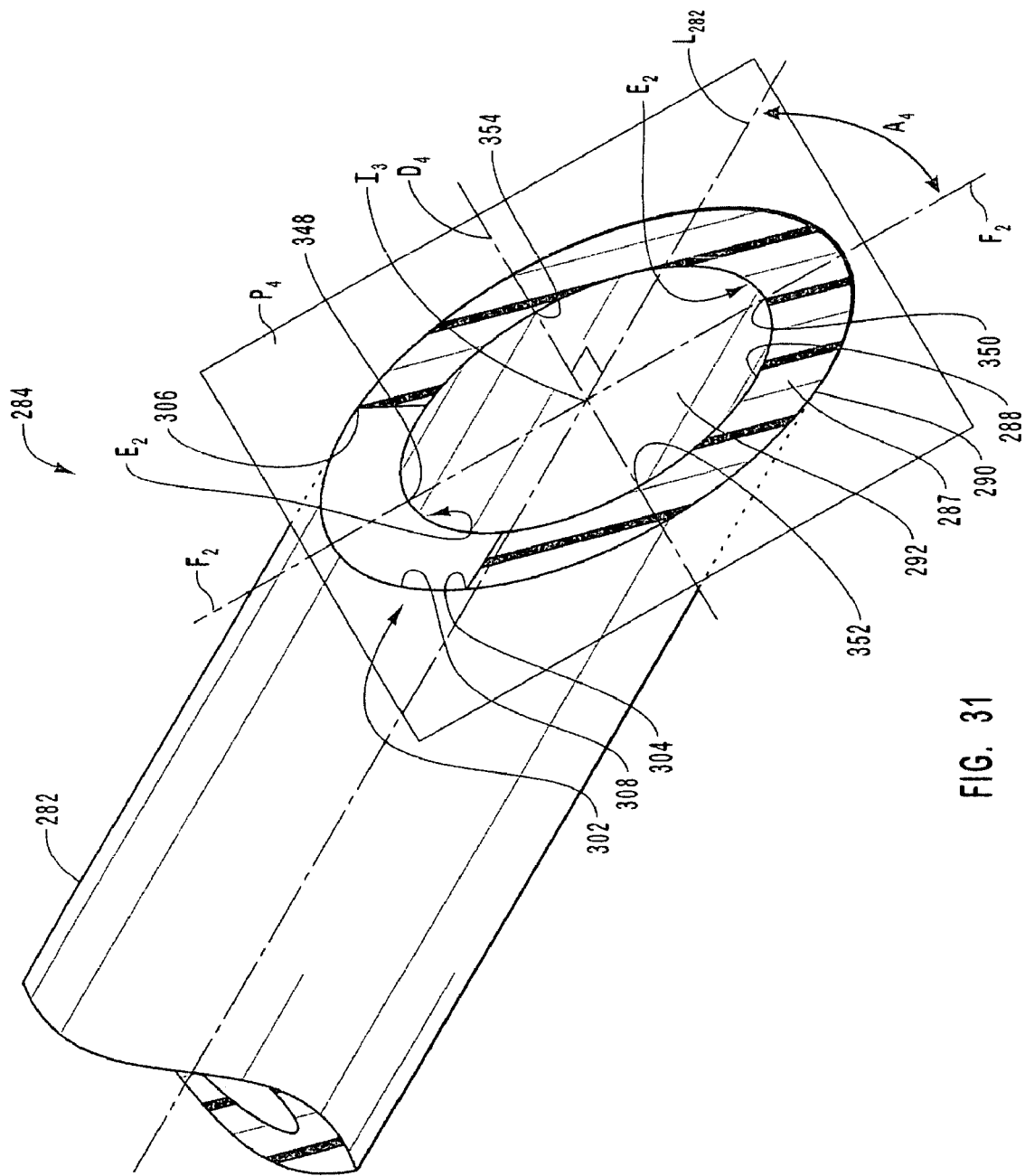
FIG. 31 is a cross-sectional view of the catheter of FIGS. 29-31 taken along section line 31-31 shown in FIGS. 29-30.

FIG. 31 is a cross-sectional view of distal portion 284 of catheter body 282 of FIGS. 28-30 taken along section line 31-31 shown in FIGS. 29 and 30. As seen in FIG. 31, proximal infusion slit orientation plane $P_4$ intersects longitudinal axis $L_{282}$ of catheter body 282 at a single slit orientation plane longitudinal positioning point $I_3$ that serves to define the longitudinal position along catheter body 282 of slit orientation plane $P_4$. Due to the inclination of slit orientation plane $P_4$ at axial deviation angle $A_4$ relative to longitudinal axis $L_{282}$ of catheter body 282, a unique diameter $D_4$ of catheter body 282 both passes through longitudinal positioning point $I_3$ and is contained in slit orientation plane $P_4$. Proximal infusion slit 302 is so disposed about longitudinal axis $L_{282}$ of catheter body 282 in proximal infusion slit orientation plane $P_4$ as to be traversed by a unique line $F_2$. Unique line $F_2$ is both contained in slit orientation plane $P_4$ and perpendicular to unique diameter $D_4$ of catheter body 282. Each of slit orientation planes $P_5$, $P_6$, and $P_7$ shown in FIG. 30 also intersect longitudinal axis $L_{282}$ of catheter body 282 at slit orientation plane longitudinal positioning points and contain unique diameters of catheter body 282 that both pass through the respective positioning points and are contained in the respective slit orientation planes.

As seen in FIG. 31, planar proximal infusion slit 302 is so disposed about longitudinal axis $L_{282}$ of catheter body 282 in slit orientation plane $P_4$ as to be traversed by unique line $F_2$. Unique line $F_2$ intersects the inner surface 288 of outer wall 287 of catheter body 282 at a first point 348 and a second point 350 that is diametrically opposite from first point 348 on the inner surface 288 of outer wall 287 of catheter body 282. At points like first point 348 and second point 350 located on unique line $F_2$, the magnitude of shear forces parallel to slit orientation plane $P_4$ that arise in outer wall 287 of catheter body 282 due to radial stress $\sigma_R$ is a maximum.

On the other hand, unique diameter $D_4$ of catheter body 282 intersects the inner surface 288 of outer wall 287 of catheter body 282 at a third point 352 and a fourth point 354 that is diametrically opposite from third point 352 on the inner surface 288 of outer wall 287 of catheter body 282. Unique line $F_2$ is coincident with the major axis of the ellipse $E_2$ formed by the intersection of inner surface 288 of catheter body 282 with $P_4$, while $D_4$ is coincident with the minor axis of the ellipse $E_2$. At points like third point 352 and fourth point 354 located on unique diameter $D_4$, the magnitude of shear forces parallel to slit orientation plane $P_4$ in outer wall 287 of catheter body 282 that arise due to radial stress $\sigma_R$ is a minimum. As the location of the proximal infusion slit 302 is moved circumferentially in either direction about longitudinal axis $L_{282}$ of catheter body 282 in slit orientation plane $P_4$ away from first point 348, the magnitude of the shear forces acting on the slit faces of infusion valve 300 that arise due to radial stress $\sigma_R$ decreases to a minimum at third point 352 and fourth point 354.

Longitudinal stress $\sigma_L$ generated in outer wall 287 of catheter body 282 when pressure differentials are created between lumen 292 and the exterior of catheter body 282 is characterized by Equation No. 4 above. Due to the inclination of slit orientation plane $P_4$ at acute axial deviation angle $A_4$ to longitudinal axis $L_{282}$ of catheter body 282, the opposing slit faces on either side of proximal infusion slit 302 are subjected to shear forces that are resolved from longitudinal stress $\sigma_L$, regardless of where proximal infusion slit 302 is disposed in slit orientation plane $P_1$ about longitudinal positioning point $I_3$. These shear forces that are resolved from longitudinal stress $\sigma_L$ also contribute to overcoming adhesion between the opposing slit faces on either side of proximal infusion slit 302 in the same manner as has been described previously in relation to FIGS. 13B and 14B.

Depending on the position of proximal infusion slit 302 in slit orientation plane $P_4$ about longitudinal axis $L_{282}$ of catheter body 82, the opposing slit faces on either side of proximal infusion slit 302 can be subjected to shear forces that are resolved from tangential stress $\sigma_T$ generated in outer wall 287 of catheter body 282 due to a pressure differential created between lumen 292 and the exterior of catheter body 282. The situation with regard to tangential stress $\sigma_T$ was discussed in detail previously in relation to FIG. 11.

Figure 32:
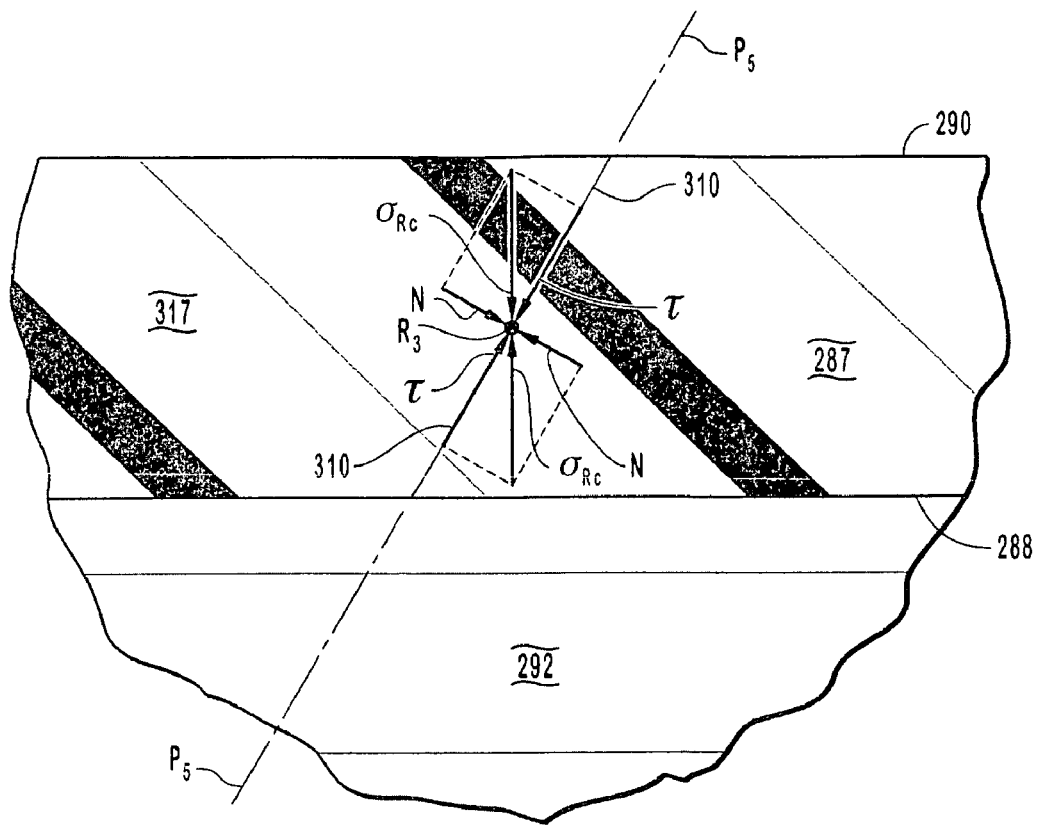
FIG. 32 is an enlarged detail view of a portion of the cross section of FIG. 30 illustrating one of the pair of slits in the infusion valve of FIGS. 28 and 29 enhanced diagrammatically to depict components of the stresses arising in the outer wall of the illustrated catheter when a positive pressure differential is created in the catheter relative to the exterior thereof.

FIG. 32 is an enlarged view of distal infusion slit 310 of FIG. 30 enhanced diagrammatically to depict resolved components of a radial compressive stress $\sigma_{Rc}$ generated in catheter body 282 when a positive pressure differential is created in lumen 292 relative to the exterior of catheter body 282. Radial compressive stress $\sigma_{Rc}$ is characterized by Equation No. 3 above. At any given point in catheter body 282, radial compressive stress $\sigma_{Rc}$ is resolvable into normal stress components and shear stress components relative to slit orientation plane $P_5$. These resolved stress components are illustrated at an idealized point $R_3$ of minimal extent that is traversed by distal infusion slit 310. At point $R_3$, radial compressive stress $\sigma_{Rc}$ is resolvable into a normal stress component N that acts perpendicular to slit orientation plane $P_5$ and a shear stress component $\tau$ that acts parallel to slit orientation plane $P_5$.

Assuming that point $R_3$ shown in FIG. 32 represents a small, finite portion of catheter body 282 at distal infusion slit 310 having known dimensions, the sum of the forces acting on point $R_3$ can be determined from the radial compressive stress $\sigma_{Rc}$ in the manner discussed previously in relation to FIGS. 13B and 14B. These forces include normal and shear forces that act on the portion of catheter body 282 contained in point $R_3$ on a first side of distal infusion slit 310 and equal and oppositely directed normal and shear forces that act on the portion of catheter body 282 contained in point $R_3$ on the opposite side of distal infusion slit 310. Similar stresses and forces are present at proximal infusion slit 302 when a positive pressure differential is created between lumen 292 and the exterior of catheter body 282. Shear forces contribute to disrupting adhesion due to intermolecular chemical bonding, intermolecular forces, and intermolecular entanglement between molecules in material at the abutting slit faces of distal infusion slit 310. The abutting slit faces are urged out of sealing abutment into oppositely directed translational motion along slit orientation plane $P_5$ by the oppositely directed shear forces. While this translational motion is so minimal as to be theoretical, it is significant on a molecular scale. This shearing process also occurs at proximal infusion slit 302 and enables active valve wall member 317 to open outwardly in response to forces acting on active valve wall member 317 generated by a positive pressure differential created between lumen 292 and the exterior of catheter body 282.

Figure 33:
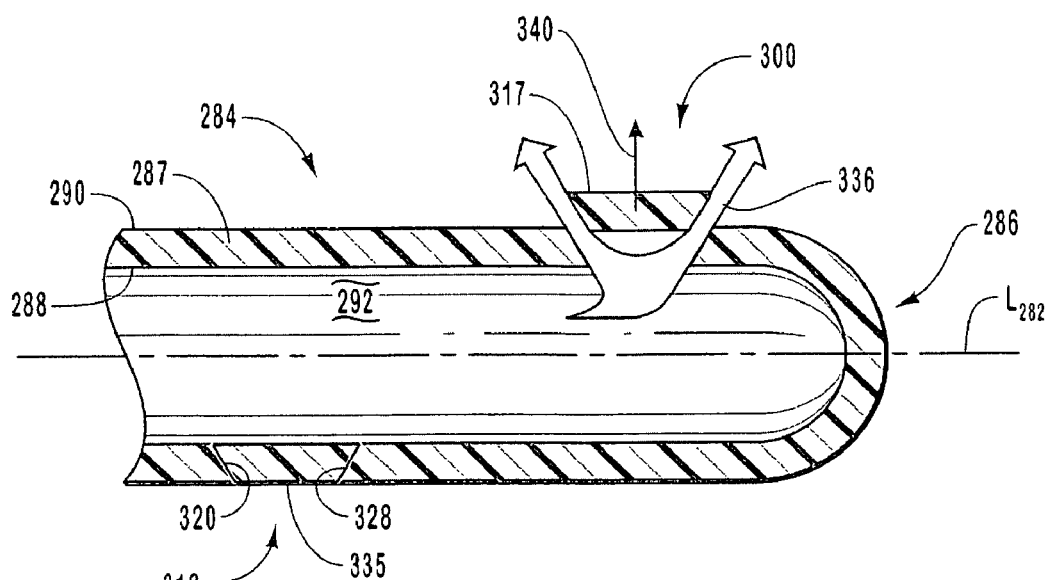
FIG. 33 is the cross section of FIG. 30 depicting the behavior of the infusion valve when a positive pressure differential is created in the illustrated catheter relative to the exterior thereof.

As shown in FIG. 33, the shear forces and their resulting stresses enable active valve wall member 317 to move in a direction indicated by arrow 340, and enables infusion valve 300 to open outwardly in response to the forces acting on catheter body 282 as a result of the imposition of a positive pressure differential between lumen 292 and the exterior of catheter body 282. Fluid 336 is shown flowing out from lumen 292 to the exterior of catheter body 282 in response to a positive pressure differential therebetween.

Figure 34:
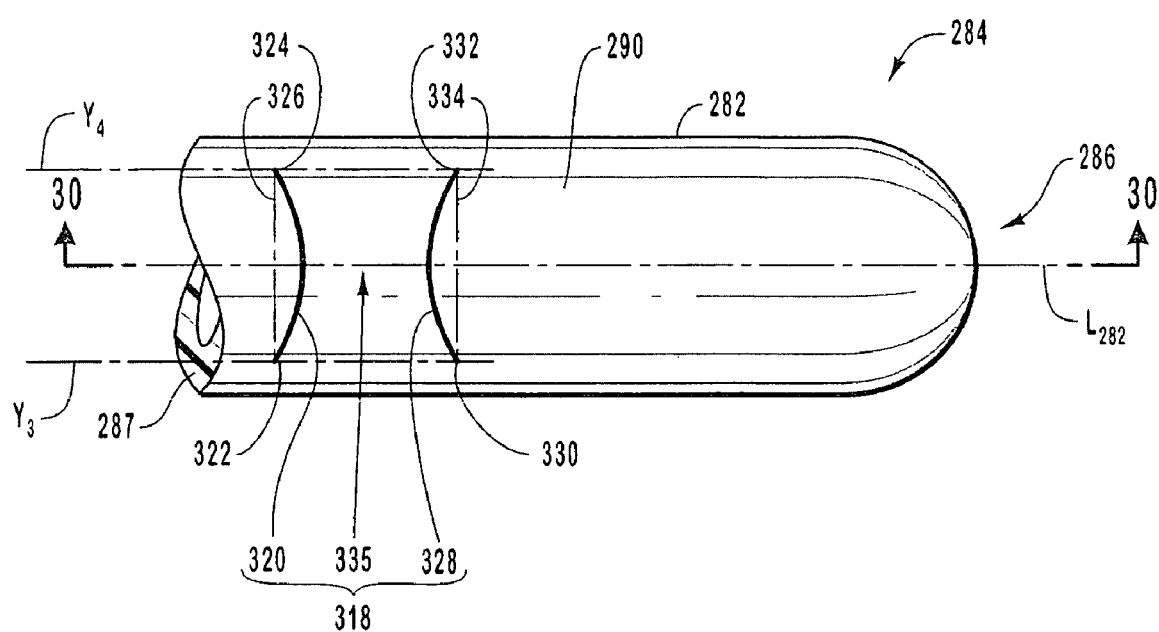
FIG. 34 is an enlarged plan view of the distal portion of a single lumen catheter showing an aspiration valve formed in the outer wall thereof that incorporates teachings of the present invention.

FIG. 34 is an enlarged plan view of distal portion 284 like that of FIG. 28 rotated approximately 180° about longitudinal axis $L_{282}$ to illustrate a thirteenth embodiment of a slit valve that incorporates teachings of the present invention and that assumes the form of a one-way, two position aspiration valve 318 formed through outer wall 287 of catheter body 282. Aspiration valve 318 includes a planar proximal aspiration slit 320 that extends on outer surface 290 of catheter body 282 between a first proximal aspiration endpoint 322 and a second proximal aspiration endpoint 324. First proximal aspiration endpoint 322 and a second proximal aspiration endpoint 324 define the endpoints of a circumferential proximal aspiration arc 326 on outer surface 290. Circumferential proximal aspiration arc 326 is disposed in a plane that contains first proximal aspiration endpoint 322 and second proximal aspiration endpoint 324 and that is perpendicular to longitudinal axis $L_{282}$ of catheter body 282. Aspiration valve 318 also includes a planar distal aspiration slit 328 that extends on outer surface 290 between a first distal aspiration endpoint 330 and a second distal aspiration endpoint 332. First distal aspiration endpoint 330 and second distal aspiration endpoint 332 define the endpoints of a circumferential distal aspiration arc 334 on outer surface 290. Circumferential distal aspiration arc 334 is disposed in a plane that contains first distal aspiration endpoint 330 and second distal aspiration endpoint 332 and that is perpendicular to longitudinal axis $L_{282}$ of catheter body 282.

First proximal aspiration endpoint 322 and first distal aspiration endpoint 330 are so located on outer surface 290 of catheter body 282 as to define therebetween on outer surface 290 a third line $Y_3$ that is parallel to longitudinal axis $L_{282}$ of catheter body 282. Second proximal aspiration endpoint 324 and second distal aspiration endpoint 332 are so located on outer surface 290 of catheter body 282 as to define therebetween on outer surface 290 a fourth line $Y_4$ that is parallel to longitudinal axis $L_{282}$ of catheter body 282. In FIG. 34, proximal aspiration slit 320 and distal aspiration slit 328 appear as laterally symmetric curves that each extend about longitudinal axis $L_{182}$ on outer surface 290 of catheter body 282 between third line $Y_3$ and fourth line $Y_4$.

A pressure differential sensitized active valve wall member 335 is integrally formed with catheter body 282 and partially circumscribed by proximal aspiration slit 320 and distal aspiration slit 328. By partially circumscribing active valve wall member 335, proximal aspiration slit 320 and distal aspiration slit 328 reduce the restraint to inward movement of active valve wall member 335 imposed by portions of catheter body 282 that are adjacent to active valve wall member 335. The portion of outer wall 287 of catheter body 282 that is disposed between proximal aspiration slit 320 and circumferential proximal aspiration arc 326 is partially circumscribed by proximal aspiration slit 320 and operates as a smaller active valve wall member. The portion of outer wall 287 of catheter body 282 that is disposed between distal aspiration slit 328 and circumferential distal aspiration arc 334 is partially circumscribed by distal aspiration slit 328 and also operates as a smaller active valve wall member.

As seen in FIG. 30, planar proximal aspiration slit 320 is contained in a proximal aspiration slit orientation plane $P_7$ that is oriented at an acute axial deviation angle $A_7$ to longitudinal axis $L_{282}$ of catheter body 282, while planar distal aspiration slit 328 is contained in a distal aspiration slit orientation plane $P_6$ that is oriented at an acute axial deviation angle $A_6$ to longitudinal axis $L_{282}$. As proximal aspiration slit orientation plane $P_7$ is not parallel to distal aspiration slit orientation plane $P_6$, proximal aspiration slit orientation plane $P_7$ is oriented at a divergence angle $A_9$ relative to distal aspiration slit orientation plane $P_6$. Broadly, acute axial deviation angle $A_6$ and acute axial deviation angle $A_7$ may be in a range from about 10° to about 80°. More narrowly, acute axial deviation angle $A_6$ and acute axial deviation angle $A_7$ may be in a range from about 20° to about 70°. Most narrowly, acute axial deviation angle $A_6$ and acute axial deviation angle $A_7$ may be in a range from about 30° to about 60°. Axial deviation angle $A_6$ may be equal to or differ from axial deviation angle $A_7$. It is not necessary that axial deviation angles $A_6$ and $A_7$ be equal to or correspond to axial deviation angles $A_4$ and $A_5$.

As shown in FIG. 30, the longitudinal cross section of active valve wall member 335 assumes a trapezoidal configuration having the longer of the parallel sides thereof on the inner surface 288 of outer wall 287 of catheter body 282 adjacent to lumen 292 and the shorter of the parallel sides thereof on the outer surface 290 of outer wall 287 of catheter body 282. This produces in the longitudinal cross section of active valve wall member 335 a wedge shape that facilitates the inward movement of active valve wall member 335 in response to a negative pressure differential, while precluding outward movement of active valve wall member 335 in response to a positive pressure differential. In this manner, aspiration valve 318 operates as an inwardly-opening one-way, two-position valve.

Figure 35:
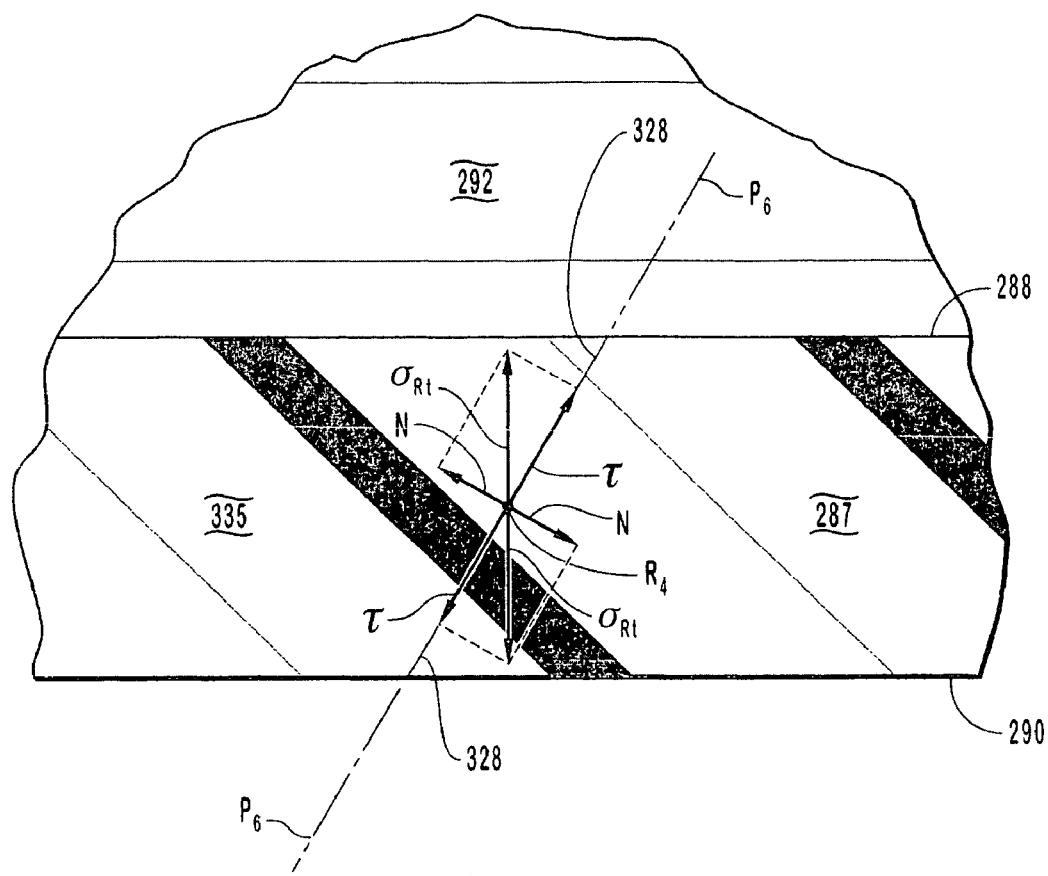
FIG. 35 is an enlarged detail view of a portion of the cross section of FIG. 30 illustrating one of the pair of slits in the aspiration valve of FIGS. 29-30, and 34 enhanced diagrammatically to depict components of the stresses arising in the outer wall of the illustrated catheter when a negative pressure differential is created in the catheter relative to the exterior thereof.

FIG. 35 is an enlarged view of distal aspiration slit 328 of FIG. 30 enhanced diagrammatically to depict resolved components of a radial tensile stress $\sigma_{Rt}$ generated in catheter body 282 when a negative pressure differential is created in catheter body 282 relative to the exterior thereof. Radial tensile stress $\sigma_{Rt}$ is characterized by Equation No. 3 above. At any given point in catheter body 282, radial tensile stress $\sigma_{Rt}$ is resolvable into normal stress components and shear stress components relative to slit orientation plane $P_6$. These resolved stress components are illustrated at an idealized point $R_4$ of minimal extent that is traversed by distal aspiration slit 328. At point $R_4$, radial tensile stress $\sigma_{Rt}$ is resolvable into a normal stress component N that acts perpendicular to slit orientation plane $P_6$ and a shear stress component $\tau$ that acts parallel to slit orientation plane $P_6$.

Assuming that point $R_4$ shown in FIG. 34 represents a small, finite portion of catheter body 282 at distal aspiration slit 328 having known dimensions, the sum of the forces acting on point $R_4$ can be determined from the radial tensile stress $\sigma_{Rt}$ in the manner discussed previously in relation to FIGS. 13B and 14B. These forces include normal and shear forces that act on the portion of catheter body 282 contained in point $R_4$ on a first side of distal aspiration slit 328, and equal and oppositely directed normal and shear forces that act on the portion of catheter body 282 contained in point $R_4$ on the opposite side of distal aspiration slit 328. Similar stresses and forces are present at proximal aspiration slit 320 when a negative pressure differential is created in catheter body 282 relative to the exterior thereof.

Shear forces and the resulting stresses contribute to overcoming adhesion between the opposing slit faces of distal aspiration slit 328 in the same manner described above in relation to FIGS. 13B and 14B. Shear forces contribute to disrupting adhesion due to intermolecular chemical bonding, intermolecular forces, and intermolecular entanglement between molecules in material at the abutting slit faces of distal aspiration slit 328. The abutting slit faces are urged out of sealing abutment into oppositely directed translational motion along slit orientation plane $P_6$ by the oppositely directed shear forces. While this translational motion is so minimal as to be theoretical, it is significant on a molecular scale. This shearing process also occurs at proximal aspiration slit 320 and enables active valve wall member 335 to open inwardly in response to forces acting on active valve wall member 335 generated by a negative pressure differential created between lumen 292 and the exterior of catheter body 282.

Figure 36:
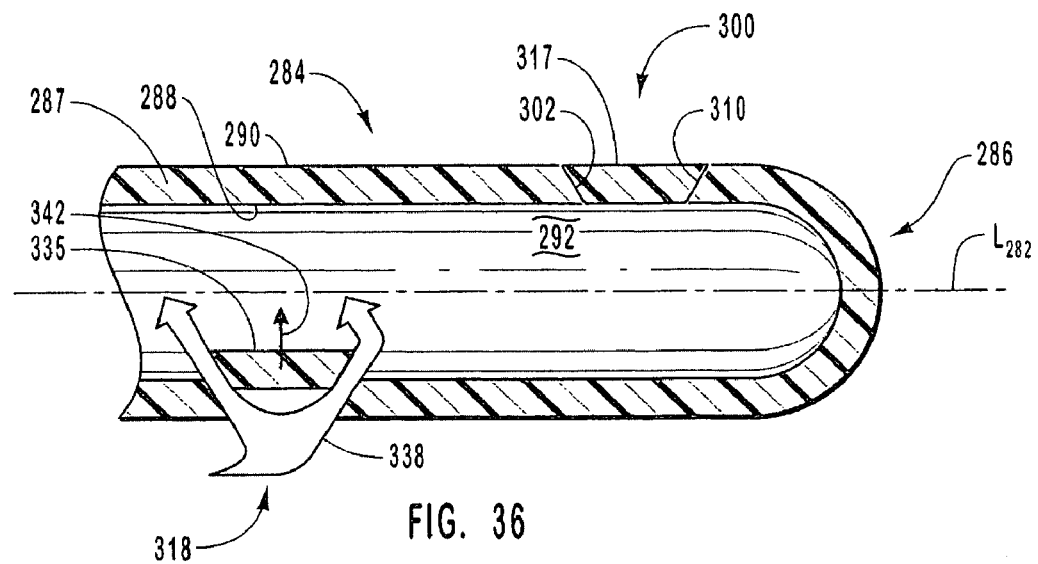
FIG. 36 is the cross section of FIG. 30 depicting the behavior of the aspiration valve when a negative pressure differential is created in the illustrated catheter relative to the exterior thereof.

As shown in FIG. 36, the shear forces and their resulting stresses enable active valve wall member 335 to move in a direction indicated by arrow 342, and enables aspiration valve 318 to open inwardly in response to the forces acting on catheter body 282 as a result of the imposition of a negative pressure differential between lumen 292 and the exterior of catheter body 282. Fluid 338 is shown flowing into lumen 292 from the exterior of catheter body 282 in response to a negative pressure differential therebetween.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A cardiovascular access catheter comprising:
   (a) an elongated catheter body enclosing a longitudinally disposed fluid flow lumen with a longitudinal axis, said catheter body having an inner surface, an outer surface, and a cylindrical outer wall therebetween of uniform thickness, and having a closed distal end, said catheter body being comprised of a polymeric elastomer material; and
   (b) a two-way, three-position valve operatively associated with said catheter body, said valve comprising a planar slit formed through said cylindrical outer wall from said outer surface to said inner surface thereof and contained in a slit orientation plane,
      (i) said slit extending between a proximal slit endpoint and a distal slit endpoint so located on said outer surface of said catheter body as to avoid defining therebetween on said outer surface a line parallel to the longitudinal axis of said catheter body, and
      (ii) said proximal slit endpoint and said distal slit endpoint being so located on said outer surface of said catheter body as to avoid defining therebetween on said outer surface an arc in a plane perpendicular to the longitudinal axis of said catheter body.

2. A catheter as recited in claim 1, wherein an angular separation of said proximal slit endpoint and said distal slit endpoint about the longitudinal axis of said catheter is in a range from about 5 to about 135 degrees.

3. A catheter as recited in claim 2, wherein the angular separation of said proximal slit endpoint and said distal slit endpoint about the longitudinal axis of said catheter is in the range from about 15 to about 125 degrees.

4. A catheter as recited in claim 3, wherein the angular separation of said proximal slit endpoint and said distal slit endpoint about the longitudinal axis of said catheter is in the range from about 25 to about 115 degrees.

5. A catheter as recited in claim 1, wherein a longitudinal separation of said proximal slit endpoint and said distal slit endpoint parallel the longitudinal axis of said catheter is in a range from about 1 to about 10 times said thickness of said outer wall of said catheter body.

6. A catheter as recited in claim 5, wherein the longitudinal separation of said proximal slit endpoint and said distal slit endpoint parallel the longitudinal axis of said catheter is in the range from about 2 to about 7.5 times said thickness of said outer wall of said catheter body.

7. A catheter as recited in claim 6, wherein the longitudinal separation of said proximal slit endpoint and said distal slit endpoint parallel the longitudinal axis of said catheter is in the range from about 3 to about 5 times said thickness of said outer wall of said catheter body.

8. A valved intravenous catheter comprising:
   (a) a flexible elongated catheter body having a closed distal end and enclosing a longitudinally disposed fluid flow lumen with a longitudinal axis, said lumen being encircled by a cylindrical outer wall of uniform thickness having an outer surface and an inner surface defining said lumen, said catheter body being comprised of a polyurethane material; and
   (b) a two-way, three-position valve operatively associated with said catheter body, said valve comprising:
      (i) a planar slit formed through said outer wall of said catheter body proximate said distal end thereof;
      (ii) a first valve wall integrally formed with said outer wall of said catheter body, said first valve wall terminating in a first slit face extending from said outer surface to said inner surface of said outer wall between a proximal slit end line and a distal slit end line, said proximal slit end line extending between an outer proximal endpoint on said outer surface of said catheter body and an inner proximal endpoint on said inner surface of said catheter body, and said distal slit end line extending between an outer distal endpoint on said outer surface and an inner distal endpoint on said inner surface; and
      (iii) a second valve wall integrally formed with said outer wall of said catheter body adjacent said first valve wall on the opposite side of said slit from said first valve wall,
         (A) said second valve wall terminating in a second slit face opposed to and congruent with said first slit face, said second slit face extending from said outer surface to said inner surface of said outer wall between said proximal slit end line and said distal slit end line,
         (B) in the closed position of said valve said first slit face engaging said second slit face in sealing abutment along a slit orientation plane disposed at an acute axial deviation angle to the longitudinal axis of said catheter body, whereby positive and negative pressure differentials created in said lumen relative to an exterior of said catheter body produce a first shear force component in said first valve wall at said first slit face and an oppositely directed second shear force component in said second valve wall at said second slit face, said first shear force component and said second shear force component urging said first slit face and said second slit face out of said sealing abutment therebetween into oppositely directed translational motion along said slit orientation plane, thereby to facilitate disruption of molecular adhesion between said polyurethane material at said first slit face and said polyurethane material at said second slit face and to enable said first valve wall and said second valve wall to open outwardly in response to said positive pressure differentials and inwardly in response to said negative pressure differentials.

9. A catheter as recited in claim 8, wherein said acute axial deviation angle is in a range from about 10 to about 80 degrees.

10. A catheter as recited in claim 9, wherein said acute axial deviation angle is in the range from about 20 to about 70 degrees.

11. A catheter as recited in claim 10, wherein said acute axial deviation angle is in the range from about 30 to about 60 degrees.

12. A catheter as recited in claim 8, wherein said slit has a length measured along a slit curve extending along said outer surface of said catheter body between said outer proximal endpoint and said outer distal endpoint, said slit length being in a range from about 1 to about 10 times said thickness of said outer wall of said catheter body.

13. A catheter as recited in claim 12, wherein said slit length is in the range from about 2 to about 7.5 times said thickness of said outer wall of said catheter body.

14. A catheter as recited in claim 13, wherein said slit length is in the range from about 3 to about 5 times said thickness of said outer wall of said catheter body.

* * * * *